(12) United States Patent
Edwards et al.

(10) Patent No.: US 6,610,054 B1
(45) Date of Patent: Aug. 26, 2003

(54) MEDICAL PROBE DEVICE AND METHOD

(75) Inventors: Stuart D. Edwards, Los Altos, CA (US); Ronald G. Lax, Grass Valley, CA (US); Ingemar H. Lundquist, Pebble Beach, CA (US); Hugh R. Sharkey, Redwood City, CA (US)

(73) Assignee: Vidamed, Inc., Fremont, CA (US)

( * ) Notice: Subject to any disclaimer, the term of this patent is extended or adjusted under 35 U.S.C. 154(b) by 0 days.

(21) Appl. No.: 08/757,282

(22) Filed: Nov. 27, 1996

Related U.S. Application Data

(63) Continuation of application No. 08/723,588, filed on Oct. 1, 1996, which is a continuation of application No. 08/618,383, filed on Mar. 20, 1996, now Pat. No. 5,800,378, which is a continuation of application No. 08/313,715, filed on Sep. 27, 1994, now Pat. No. 5,531,676, which is a continuation of application No. 08/012,370, filed on Feb. 2, 1993, now Pat. No. 5,370,675, which is a continuation-in-part of application No. 07/929,638, filed on Aug. 12, 1992, now abandoned.

(51) Int. Cl.[7] .............................................. A61B 17/36
(52) U.S. Cl. .......................................... 606/41; 606/42
(58) Field of Search ........................ 604/19–22; 606/33, 606/39, 41, 42, 45; 607/100–102; 128/642, 734

(56) References Cited

U.S. PATENT DOCUMENTS 5,562,703 A * 10/1996 Desai ........................ 606/210

* cited by examiner

Primary Examiner—Mark Bockelman
(74) Attorney, Agent, or Firm—Lyon & Lyon LLP

(57) ABSTRACT

A medical probe device comprises a catheter having a stylet guide housing with one or more stylet ports in a side wall thereof and a stylet guide for directing a flexible stylet outward through the stylet port and through intervening tissue at a preselected, adjustable angle to a target tissue. The total catheter assembly includes a stylet guide lumen communicating with the stylet port and a stylet positioned in said stylet guide lumen for longitudinal movement from the port through intervening tissue to a target tissue. The stylet can be an electrical conductor enclosed within a non-conductive layer, the electrical conductor being a radiofrequency electrode. Preferably, the non-conductive layer is a sleeve which is axially moveable on the electrical conductor to expose a selected portion of the electrical conductor surface in the target tissue. The stylet can also be a microwave antenna. The stylet can also be a hollow tube for delivering treatment fluid to the target tissue. It can also include a fiber optic cable for laser treatment. The catheter can include one or more inflatable balloons located adjacent to the stylet port for anchoring the catheter or dilation. Ultrasound transponders and temperature sensors can be attached to the probe end and/or stylet. The stylet guide can define a stylet path from an axial orientation in the catheter through a curved portion to a lateral orientation at the stylet port.

8 Claims, 28 Drawing Sheets

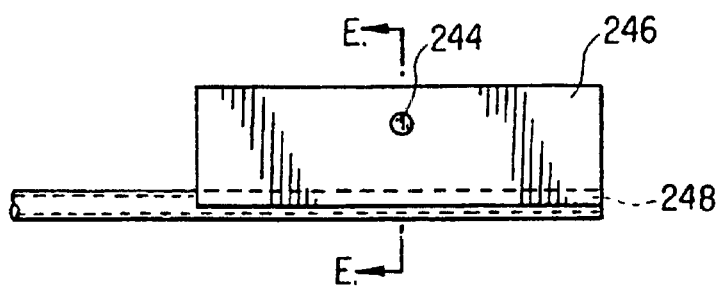
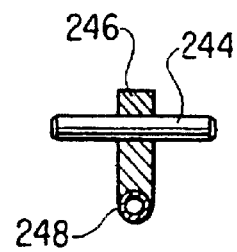
FIG. 21    FIG. 22
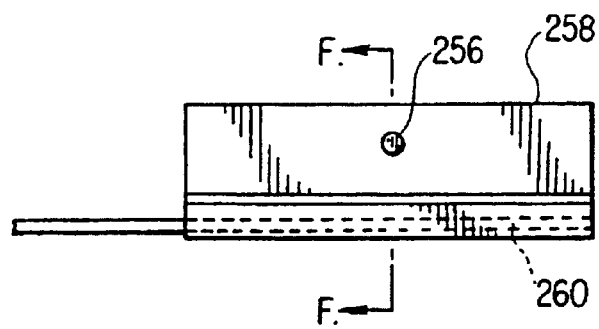
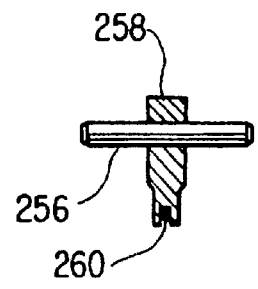
FIG. 23    FIG. 24
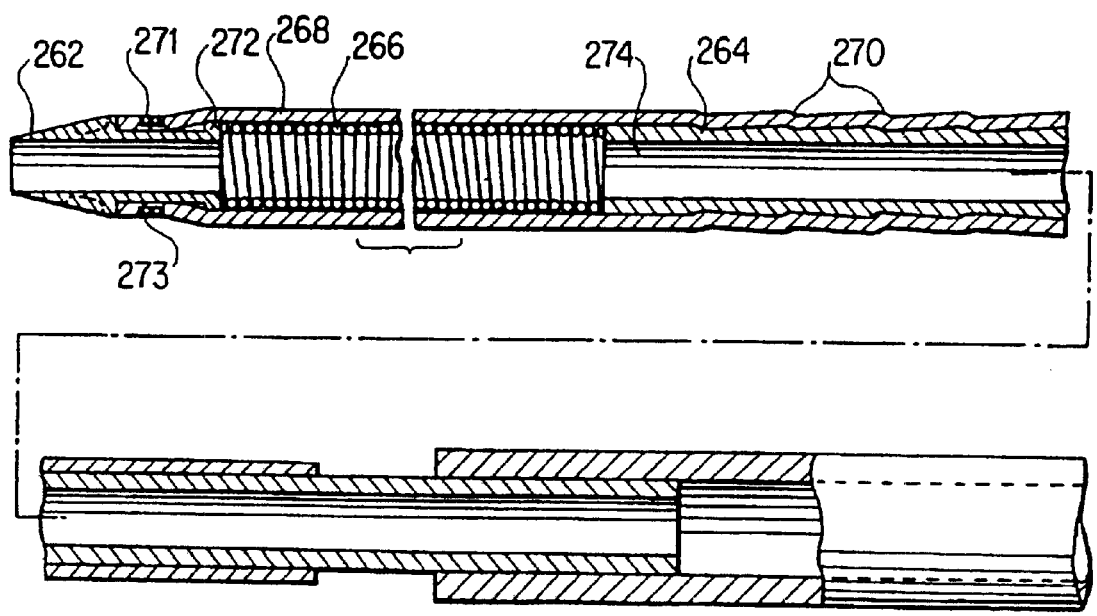
FIG. 25

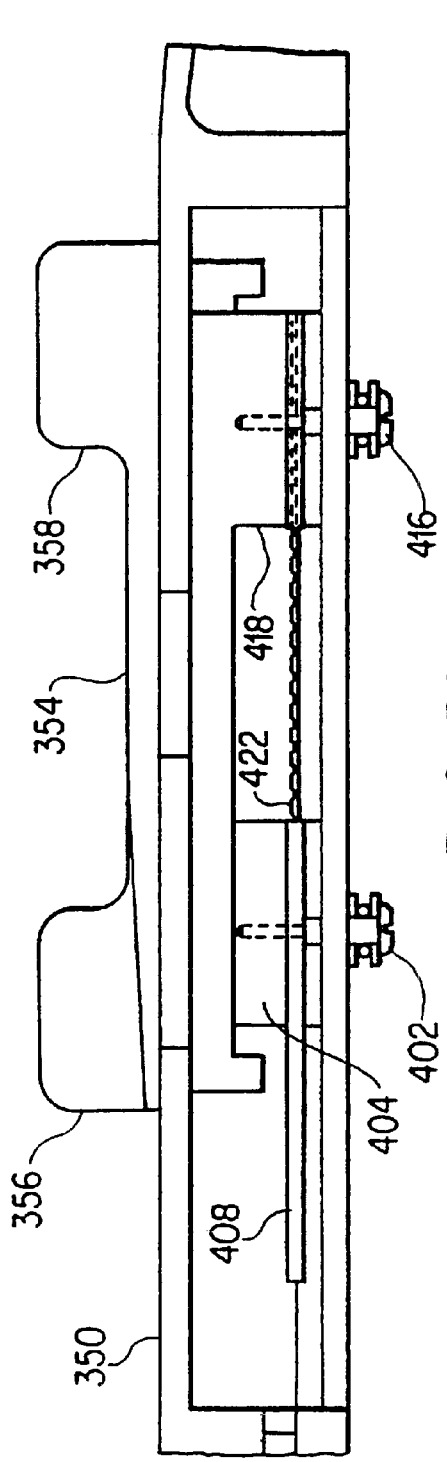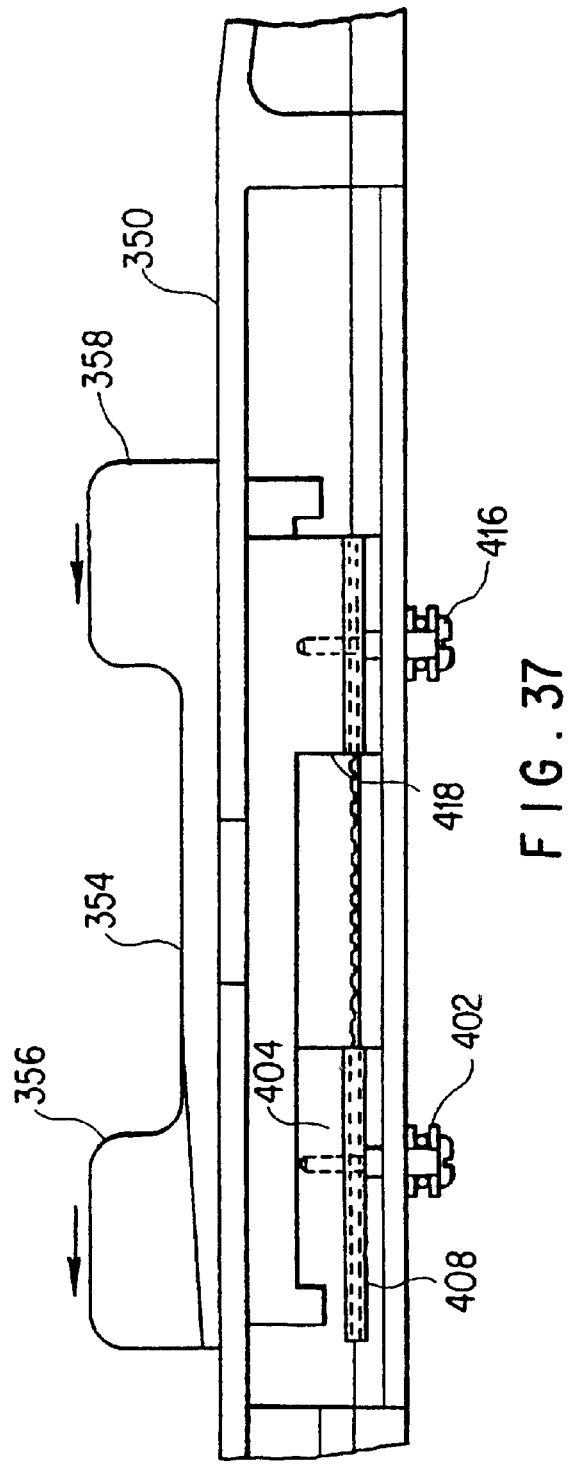

MEDICAL PROBE DEVICE AND METHOD

RELATIONSHIP TO COPENDING APPLICATION

This is a continuation of U.S. application Ser. No. 08/723,588, filed Oct. 1, 1996, which is in turn a continuation of U.S. application Ser. No. 08/618,383, filed Mar. 20, 1996 now U.S. Pat. No. 5,800,378, which is in turn a continuation of U.S. application Ser. No. 08/313,715, filed Sep. 27, 1994 now U.S. Pat. No. 5,531,676, which is in turn a continuation of U.S. application Ser. No. 08/012,370, filed Feb. 2, 1993 now U.S. Pat. No. 5,370,675, which is a continuation-in-part of U.S. application Ser. No. 07/929,638, filed Aug. 12, 1992 abandoned, which are incorporated herein by reference as if set forth in full.

FIELD OF THE INVENTION

This invention is directed to a unique device and method for penetrating body tissues for medical purposes such as tissue destruction and fluid substance delivery, for example. The device penetrates tissue to the precise target selected in order to deliver energy to the tissue and/or deliver substances. It limits this activity to the precise preselected site, thereby minimizing trauma to normal surrounding tissue and achieving a greater medical benefit. This device is a catheter-like device for positioning a treatment assembly in the area or organ selected for medical treatment with one or more stylets in the catheter, mounted for extension from a stylet port in the side of the catheter through surrounding tissue to the tissue targeted for medical activity.

BACKGROUND OF THE INVENTION

Treatment of cellular tissues usually requires direct contact of target tissue with a medical instrument, usually by surgical procedures exposing both the target and intervening tissue to substantial trauma. Often, precise placement of a treatment probe is difficult because of the location of a target tissue in the body or the proximity of the target tissue to easily damaged, critical body organs, nerves, or other components.

Benign prostatic hypertrophy or hyperplasia (BPH), for example, is one of the most common medical problems experienced by men over 50 years old. Urinary tract obstruction due to prostatic hyperplasia has been recognized since the earliest days of medicine. Hyperplastic enlargement of the prostate gland often leads to compression of the urethra, resulting in obstruction of the urinary tract and the subsequent development of symptoms including frequent urination, decrease in urinary flow, nocturia, pain, discomfort, and dribbling. The association of BPH with aging has been shown to exceed 50% in men over 50 years of age and increases in incidence to over 75% in men over 80 years of age. Symptoms of urinary obstruction occur most frequently between the ages of 65 and 70 when approximately 65% of men in this age group have prostatic enlargement.

Currently there is no proven effective nonsurgical method of treatment of BPH. In addition, the surgical procedures available are not totally satisfactory. Currently patients suffering from the obstructive symptoms of this disease are provided with few options: continue to cope with the symptoms (i.e., conservative management), submit to drug therapy at early stages, or submit to surgical intervention. More than 430,000 patients per year undergo surgery for removal of prostatic tissue in the United States. These represent less than five percent of men exhibiting clinical significant symptoms.

Those suffering from BPH are often elderly men, many with additional health problems which increase the risk of surgical procedures. Surgical procedures for the removal of prostatic tissue are associated with a number of hazards including anesthesia associated morbidity, hemorrhage, coagulopathies, pulmonary emboli and electrolyte imbalances. These procedures performed currently can also lead to cardiac complications, bladder perforation, incontinence, infection, urethral or bladder neck stricture, retention of prostatic chips, retrograde ejaculation, and infertility. Due to the extensive invasive nature of the current treatment options for obstructive uropathy, the majority of patients delay definitive treatment of their condition. This circumstance can lead to serious damage to structures secondary to the obstructive lesion in the prostate (bladder hypertrophy, hydronephrosis, dilation of the kidney pelves, etc.) which is not without significant consequences. In addition, a significant number of patients with symptoms sufficiently severe to warrant surgical intervention are poor operative risks and are poor candidates for prostatectomy. In addition, younger men suffering from BPH who do not desire to risk complications such as infertility are often forced to avoid surgical intervention. Thus the need, importance and value of improved surgical and non-surgical methods for treating BPH is unquestionable.

High-frequency currents are used in electrocautery procedures for cutting human tissue especially when a bloodless incision is desired or when the operating site is not accessible with a normal scalpel but presents an access for a thin instrument through natural body openings such as the esophagus, intestines or urethra. Examples include the removal of prostatic adenomas, bladder tumors or intestinal polyps. In such cases, the high-frequency current is fed by a surgical probe into the tissue to be cut. The resulting dissipated heat causes boiling and vaporization of the cell fluid at this point, whereupon the cell walls rupture and the tissue is separated.

Destruction of cellular tissues in situ has been used in the treatment of many diseases and medical conditions alone or as an adjunct to surgical removal procedures. It is often less traumatic than surgical procedures and may be the only alternative where other procedures are unsafe. Ablative treatment devices have the advantage of using a destructive energy which is rapidly dissipated and reduced to a non-destructive level by conduction and convection forces of circulating fluids and other natural body processes.

Microwave, radiofrequency, acoustical (ultrasound) and light energy (laser) devices, and tissue destructive substances have been used to destroy malignant, benign and other types of cells and tissues from a wide variety of anatomic sites and organs. Tissues treated include isolated carcinoma masses and, more specifically, organs such as the prostate, glandular and stromal nodules characteristic of benign prostate hyperplasia. These devices typically include a catheter or cannula which is used to carry a radiofrequency electrode or microwave antenna through a duct to the zone of treatment and apply energy diffusely through the duct wall into the surrounding tissue in all directions. Severe trauma is often sustained by the duct wall during this cellular destruction process, and some devices combine cooling systems with microwave antennas to reduce trauma to the ductal wall. For treating the prostate with these devices, for example, heat energy is delivered through the walls of the urethra into the surrounding prostate cells in an effort to kill the tissue constricting the urethra. Light energy, typically from a laser, is delivered to prostate tissue target sites by "burning through" the wall of the urethra. Healthy cells of the duct wall and healthy tissue between the nodules and duct wall are also indiscriminately destroyed in the process and can cause unnecessary loss of some prostate function. Furthermore, the added cooling function of some microwave devices complicates the apparatus and requires that the device be sufficiently large to accommodate this cooling system.

Application of liquids to specific tissues for medical purposes is limited by the ability to obtain delivery without traumatizing intervening tissue and to effect a delivery limited to the specific target tissue. Localized chemotherapy, drug infusions, collagen injections, or injections of agents which are then activated by light, heat or chemicals would be greatly facilitated by a device which could conveniently and precisely place a fluid supply catheter opening at the specific target tissue.

OBJECTS AND SUMMARY OF THE INVENTION

It is the principal object of this invention to provide a device and method for penetrating tissue, through intervening tissues to the precise target tissue selected for a medical action such as tissue destruction and/or substance delivery, limiting this activity to the precise preselected site, thereby minimizing the trauma and achieving a greater medical benefit.

One principal object of this invention is to provide a device and method for tissue destruction of body tissues which delivers the therapeutic energy directly into a target tissue while minimizing effects on its surrounding tissue.

Another principal object of this invention is to provide a device and method for introducing fluid treatment agents, particularly flowable liquids, with greater precision and ease to a specific location in the body.

Another object of this invention is to provide a thermal destruction device which gives the operator more information about the temperature and other conditions created in both the tissue targeted for treatment and the surrounding tissue. In addition, it will provide more control over the physical placement of the stylet and over the parameters of the tissue destruction process.

In summary, the medical probe device of this invention comprises a catheter having a control end and a probe end. The probe end includes a stylet guide housing having at least one stylet port in a side wall thereof and guide means for directing a flexible stylet outward through the stylet port and through intervening tissue at a preselected angle to a target tissue. The housing can include an array of such ports. The preselected angle is preferably from 20° to 160° with the central axis of the stylet guide housing. The total catheter assembly includes one or more stylet guide lumena communicating with respective stylet ports and a stylet positioned in each of said stylet guide lumena for longitudinal movement from the respective port through intervening tissue to target tissues.

The stylet can be an electrical conductor enclosed within a non-conductive layer, the electrical conductor being an radiofrequency electrode. Preferably, the non-conductive layer is a sleeve which is axially or longitudinally moveable on the electrical conductor to expose a selected portion of the electrical conductor surface in the target tissue. The stylet can also be a microwave antenna.

In a still further embodiment, the stylet is a cannula having a longitudinal, central treatment fluid supply lumen extending therethrough, and the catheter has a treatment fluid transport lumen communicating with the treatment fluid supply lumen.

An ultrasound reflector such as a bubble or an ultrasound transducer can be embedded or otherwise attached to the probe end or a portion of the stylet to provide a signal for use in positioning the catheter and stylet.

When the stylet includes a radiofrequency electrode or microwave antenna, optimally, at least one temperature sensor such as a thermistor or fiber optic cable can be attached to the probe end, stylet guide housing and/or stylet.

In one preferred embodiment, the stylet guide defines a stylet path from an axial orientation in the catheter through a curved portion to a lateral orientation at the stylet port, the curved path optionally having a radius which is sufficient to deflect the deployed, extended stylet to the desired angle, that is, a radius of up to 0.5 cm, depending upon the diameter of the catheter. The stylet guide means can define a stylet path having a first curved portion extending in a direction away from the stylet port and a second curved portion, continuing from the first curved portion and extending to the stylet port.

For deploying a plurality of stylets, the stylet guide means can define at least two non-intersecting stylet paths from parallel axial orientations in the catheter through curved portions to lateral orientations at stylet ports, the stylet ports having axes forming an angle of up to 180°. For treating prostate lobes in one embodiment, the stylet port axes form an angle of less than 90° and preferably from 50° to 70°.

The non-conductive sleeve can comprise a leading tip, a rigid proximal control section, and a flexible portion extending from the leading tip the rigid proximal control section, whereby the sleeve can be extended through a curved path from an axial orientation to an orientation extending outward through a stylet port. The leading tip can be tapered inward toward its terminal end. The flexible portion can optionally be a spiral coil. If the spiral coil is made of conductive material, it can be enclosed in an outer non-conductive material.

The distal portion of the catheter can be more flexible than the proximal portion thereof, facilitating its passage through curved ducts.

In one embodiment, a control handle is attached to the control end of the catheter and stylet movement means attached to a stylet and engaging the handle for longitudinal movement of the stylet in the stylet guide means. The stylet movement means comprises manual engagement means for translating manual motion into longitudinal motion of the stylet in the stylet guide means.

In embodiments where the electrical conductor has axial movement in the non-conductive sleeve, a non-conductive sleeve movement means is attached to a non-conductive sleeve and an electrical conductor movement means is attached to the electrical conductor enclosed therein. The non-conductive sleeve movement means translates manual motion into longitudinal motion of the non-conductive sleeve in the stylet guide means. The electrical conductor movement means translates manual motion into longitudinal motion of the electrical conductor in the non-conductive sleeve. The non-conductive sleeve movement means and the electrical conductor movement means engage the handle for movement thereon. The non-conductive sleeve movement means and the electrical conductor movement means can include separate, adjacent manual movement means, mounted on the handle for both separate and coordinated movement thereon. The housing can have at least two parallel longitudinal slots through a wall thereof, the manual movement means each including a finger engaging surface connected to a slide extending through one of the longitudinal slots to a connector in the interior of the housing, the connector being attached to a respective non-conductive sleeve or electrical conductor.

The method of this invention for applying destructive energy to a target tissue comprises first introducing a catheter to a zone adjacent to the tissue to be treated. Then an electrical conductor is moved from the catheter through surrounding tissue into a target tissue to be destroyed. The electrical conductor can be a wire or tube comprising a conductive surface surrounded by a non-conductive sleeve for preventing significant transfer of energy from the conductor in tissue surrounding the sleeve. Heat is generated in the target tissue-from an electric current or electromagnetic field produced by the electrical conductor. The volume of tissue being treated is controlled by moving the non-conductive sleeve to expose a selected length of electrode in the body tissue to be treated, the remaining area of the electrode remaining shielded by the sleeve to protect the intervening tissues. The amount and duration of the energy delivery is also varied to control the volume of tissue being treated.

The electrical conductor can be positioned using a fiber optic viewing system incorporated within the catheter shaft, positioned to facilitate positioning of the device. Such a system can also include separate optics for lumination and viewing, and flushing fluid supply conduits for flushing the viewing fields.

The electrical conductor can also be positioned in the tissue to be treated using ultrasound imaging from an ultrasound transducer positioned at a distance from the target tissue or supported by the electrical conductor or non-conducting sleeve.

The extent of heating can be monitored and controlled during the ablative treatment using temperature sensors supported by the electrical conductor or non-conductive sleeve.

In another embodiment of the method of this invention for treating a target tissue such as the prostate, two flexible stylets from the catheter are moved through catheter ports in the sidewall of the catheter and through the urethra wall and surrounding tissue into the prostate target tissue to be treated, the catheter ports having axes forming an angle of less than 180° and for treatment in some tissue, less than 90°.

In a still further embodiment, a grounding plate is placed on the skin to direct the electrical current passing from one or more electrodes in a path through the target tissue to be ablated.

BRIEF DESCRIPTION OF THE DRAWINGS

FIG. 21 is a side view of the non-conductive sleeve connector of the embodiment show in FIGS. 18 and 19.

FIG. 22 is a cross-sectional view of the non-conductive sleeve connector shown in FIG. 21, taken along the line E—E.

FIG. 23 is a side view of the electrical conductor connector of the embodiment shown in FIGS. 18 and 20.

FIG. 24 is a cross-sectional view of the electrical conductor connector shown in FIG. 23, taken along the line F—F.

FIG. 25 is a cross-sectional view of the distal end of the non-conductive sleeve shown in FIGS. 15 and 16, taken along its central axis.

FIG. 36 is a cross-section view of the central portion of the handle portion shown in FIG. 33 in the stylet and sleeve retracted position.

FIG. 37 is a cross-sectional view of the central portion of the handle portion shown in FIG. 33 with the stylet and sleeve in an extended position.

DETAILED DESCRIPTION OF THE INVENTION

Figure 1:
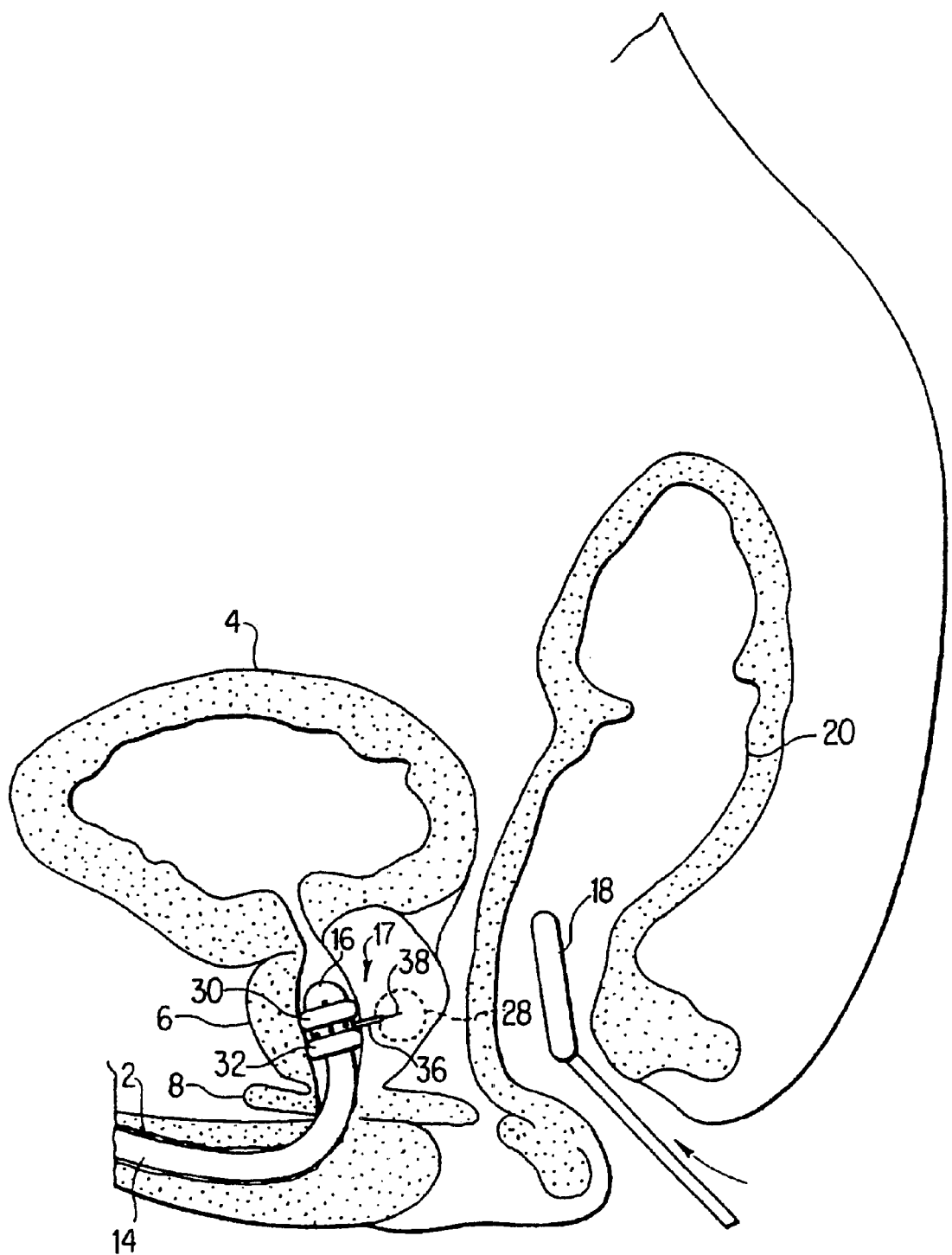
FIG. 1 is a schematic cross-sectional drawing of the lower male anatomy with one embodiment of the device of this invention in position for treatment.

The device of this invention provides a precise controlled positioning of a treatment stylet in a tissue targeted for treatment, destruction or sampling from a catheter positioned in the vicinity of the target tissue.

The term "stylet" as used hereinafter is defined to include both solid and hollow probes which are adapted to be passed from a catheter port through normal tissue to a target tissue. The stylet is shaped to facilitate easy passage through tissue. It can be a solid wire, thin rod, or other solid shape or it can be a thin hollow tube or other shape having a longitudinal lumen for introducing fluids to or removing materials from a site. The stylet can also be a thin hollow tube or other hollow shape, the hollow lumen thereof containing a reinforcing or functional rod or tube such as a laser fiberoptic cable. The stylet preferably has a sharpened end to reduce resistance and trauma when it is pushed through tissue to a target site.

The stylet can be designed to provide a variety of medically desired treatments of a selected tissue. As a radiofrequency electrode or microwave antenna, it can be used to ablate or destroy the target tissue. As a hollow tube, it can be used to deliver a treatment fluid such as a liquid to a target tissue. The liquid can be a simple solution or a suspension of solids, for example, colloidal particles, in a liquid. Since the stylet is very thin, it can be directed from the catheter through intervening normal tissue with a minimum of trauma to the normal tissue.

The device and method of this invention provide a more precise, controlled medical treatment which is suitable for destroying cells of medically targeted tissues throughout the body, both within and external to body organs. The device and method are particularly useful for treating benign prostate hyperplasia (BPH), and the device and its use are hereinafter described with respect to BPH, for purposes of simplifying the description thereof. It will be readily apparent to a person skilled in the art that the device and method can be used to destroy body tissues in any body cavities or tissue locations that are accessible by percutaneous or endoscopic catheters, and is not limited to the prostate. Application of the device and method in all of these organs and tissues are intended to be included within the scope of this invention.

BPH is a condition which arises from the benign replication and growth of cells in the prostate, forming glandular and stromal nodules which expand the prostate and constrict the opening of the prostatic urethra. Glandular nodules are primarily concentrated within the transition zone, and stromal nodules within the periurethral region. Traditional treatments of this condition have included surgical removal of the entire prostate gland, digital removal of the adenoma, as well as transurethral resection of the urethral canal and prostate to remove tissue and widen the passageway. One significant and serious complication associated with the latter method is iatrogenic sterility. More recently, laser treatment has been employed to remove tissue, limiting bleeding and loss of body fluids. Balloons have also been expanded within the urethra to enlarge its diameter, with and without heat, but have been found to have significant limitations.

Microwave therapy has been provided with some success by positioning a microwave antenna within the prostatic urethra and generating heat in the tissue surrounding the urethra with a microwave field. Coolants are sometimes applied within the catheter shaft to reduce the temperature of the urethral wall. This necessitates complicated mechanisms to provide both cooling of the immediately adjacent tissues while generating heat in the more distant prostatic tissue. This technique is similar to microwave hyperthermia. Similarly, radiofrequency tissue destruction with electrodes positioned within the urethra has limited applicability since it necessarily exposes the urethral wall to destructive temperatures. To avoid this, low temperature settings required to protect the urethra must be so low that the treatment time required to produce any useful effect is unduly extended, e.g. up to three hours of energy application.

One embodiment of the device of this invention uses the urethra to access the prostate and positions RF electrode stylets directly into the tissues or nodules to be destroyed. The portion of the stylet conductor extending from the urethra to the target tissue is enclosed within a longitudinally adjustable sleeve shield which prevents exposure of the tissue adjacent to the sleeve to the RF current. Thus the ablative destruction is confined to the tissues targeted for destruction, namely those causing the constriction. Other aspects of the invention will become apparent from the drawings and accompanying descriptions of the device and method of this invention. It will be readily apparent to a person skilled in the art that this procedure can be used in many areas of the body for percutaneous approaches and approaches through body orifices.

FIG. 1 is a schematic cross-sectional drawing of the lower male anatomy during use of the device and method of this invention. The urethra 2 extends from the urinary bladder 4 through the prostate 6 and urogenital diaphragm 8. BPH is a condition characterized by constriction of the portion of the prostatic urethra caused primarily by proliferation of benign glandular and stroma cells in the prostate. These nodules press the wall of the urethra inwardly, restricting the urethral diameter, and can press normal tissue outwardly, possibly enlarging the prostate. Traditional treatments short of removal of the prostate have included either removal of tissue from the urethra to enlarge its lumen by resection or laser tissue destruction, or by expansion and heating of the tissue surrounding the urethra to a temperature which causes cell death. The latter method is intended to reduce the swelling or enlargement of the prostate, and restore the urinary passage to at least a portion of its former diameter.

In the method of this invention, a catheter 14 with a stylet guide 16 is passed upwardly through the urethra into the prostate. The position of the guide 16 is precisely controlled, using an ultrasound image, for example, obtained from signals received from the conventional ultrasound transducer 18 inserted into the rectum 20 adjacent to the prostate through the anal opening 22. The guide facilitates easy positioning of the stylet 17 into a precise location under ultrasound imaging. Optionally, fiber optics can be used to position the stylet guide.

The terminal portion of the catheter 14 can optionally have one or more dilation balloons 30 and 32. Stylet sleeve 36 can be extended through the urethra and other tissue to be protected, and an RF electrode 38, as shown for example in this figure, can be extended deep into the target tissue 28.

Figure 3:
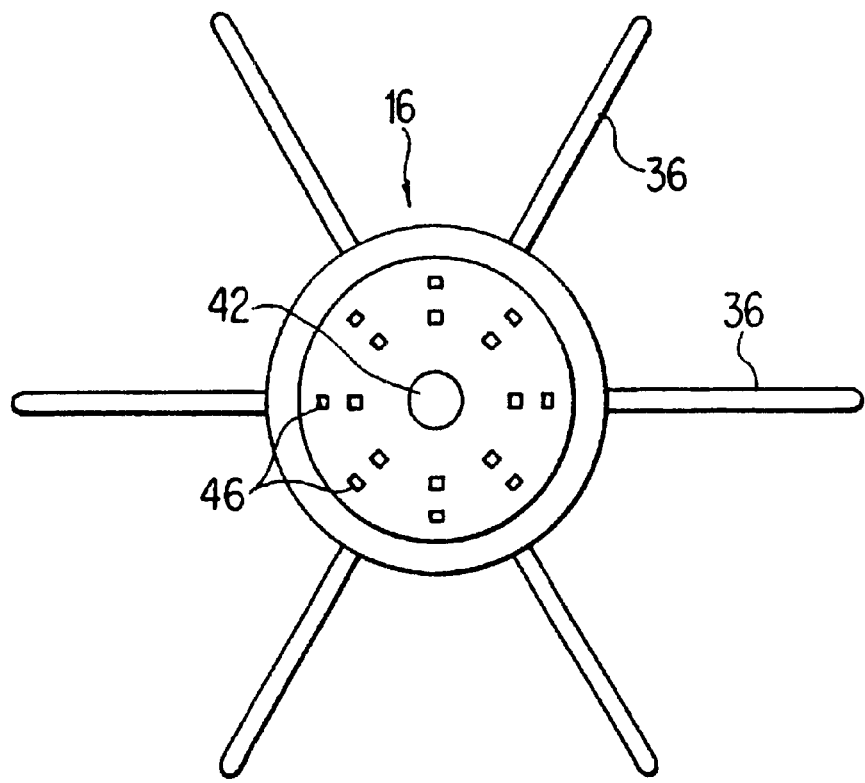
FIG. 3 is an end view of the terminal housing portion shown in FIG. 2.
Figure 2:
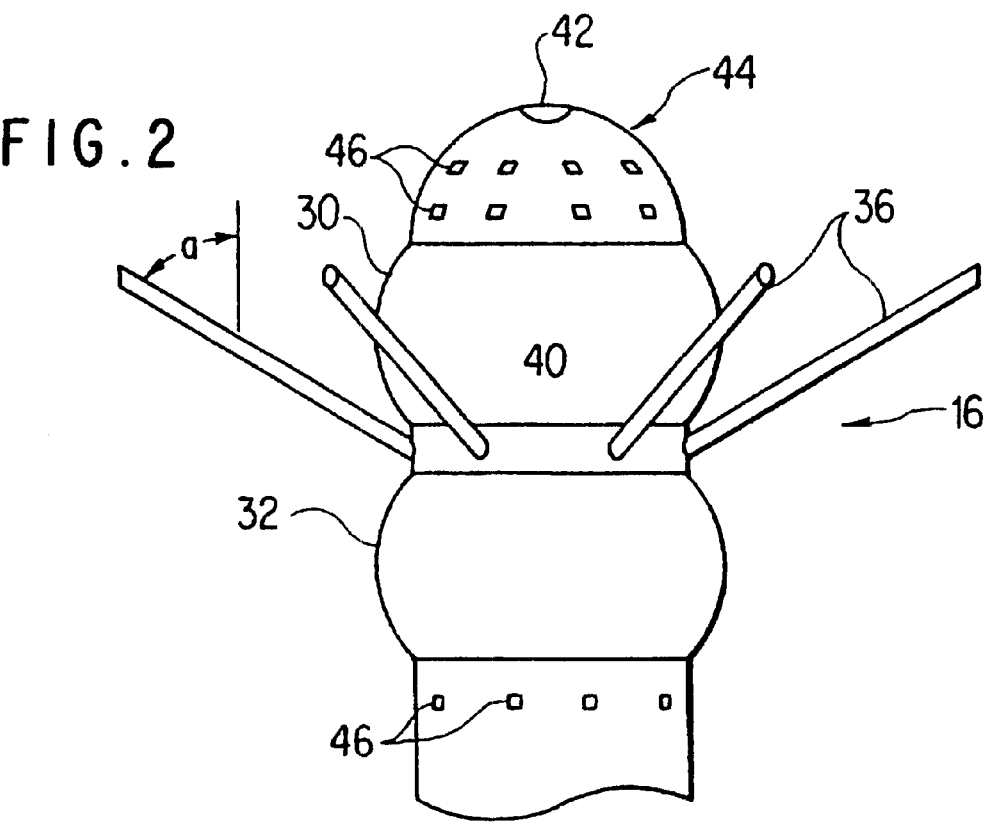
FIG. 2 is a side view of the terminal housing portion of the catheter of this invention with a plurality of extended stylets.

FIG. 2 is a side view and FIG. 3 is an end view of the terminal portion of one embodiment of a catheter of this invention. One or more stylet ports 40 are positioned between the unexpanded annular balloons 30 and 32. An ultrasound transponder 42 can be positioned at the terminal end 44 for producing signals and images which can be used for precise positioning of the stylet guide housing 16 in the prostate. Alternatively, an echogenic bubble can be incorporated into the distal housing to aid in sonographic location of the stylet guide. One or more temperature sensors 46, which can be conventional thermistors, thermocouples or optical fibers, are positioned along the catheter to provide a temperature profile of the urethra adjacent to and preferably on both sides the stylet section. This temperature profile can be used by the operator to prevent the temperature of the urethral wall from reaching a level which would cause cell destruction. These figures show both balloon segments 30 and 32 and six stylets 36 in an extended position.

The catheter can be rotated about its central axis prior to stylet deployment to orient one or more of the stylets toward tissues to be treated. After the catheter terminal housing 16 is advanced to a treatment position in the prostatic urethra, the annular balloons 30 and 32 can be expanded in the urethra to stabilize the catheter and dilate the urethral lumen. The stylets are extended through the urethral wall and intermediate tissue until they are positioned in the tissue targeted for treatment. The tissue targeted for BPH treatment may be nodules, normal tissue or both. The stylet passageways leading to ports 40 have an orientation such that their terminal axis forms an angle "a" which can be from about 20° to 160° and preferably from about 30° to 150° with the central axis of the catheter in a plane therethrough. As will be explained in greater detail hereinafter with regard to one embodiment of this invention, a non-conducting sleeve is then moved to expose the target tissue to controlled heating by an electric current or an electromagnetic field to a destructive temperature above 45° C. and preferably within the range of from 55° to 99° C.

Figure 4:
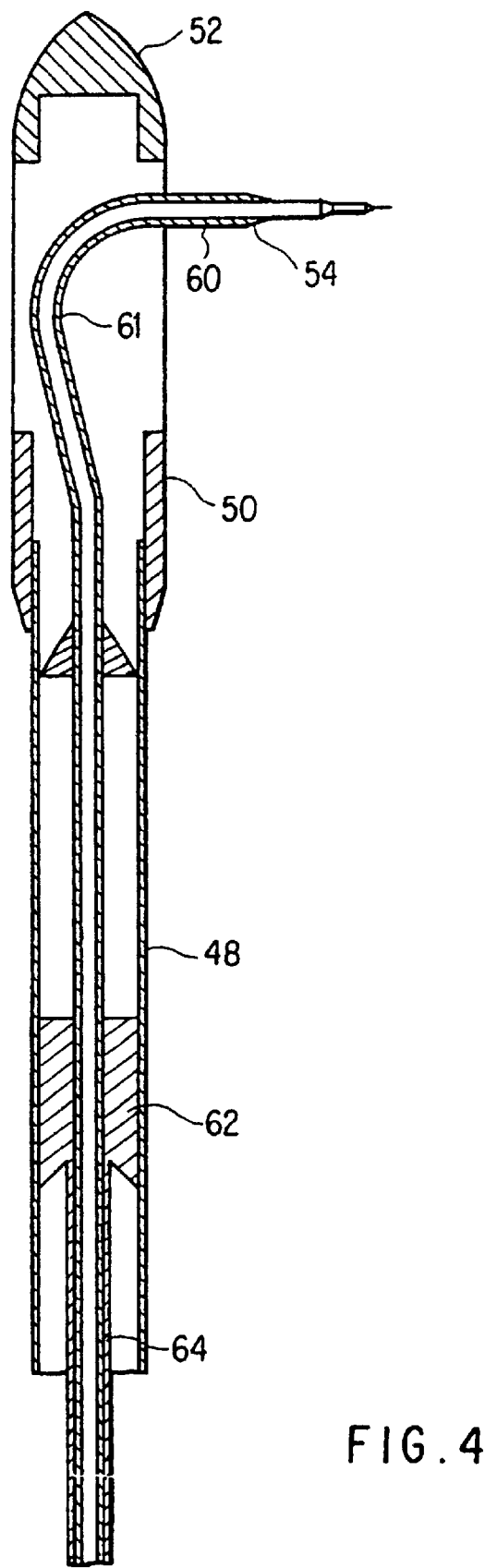
FIG. 4 is a cross-sectional view of an alternative embodiment of the catheter of this invention.
Figure 5:
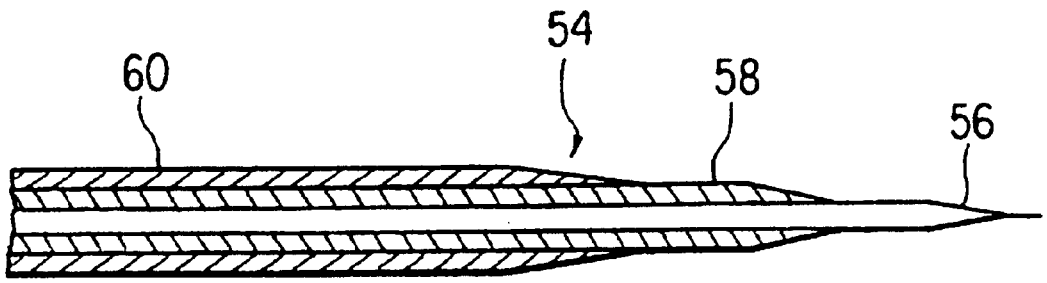
FIG. 5 is a cross-sectional representation of an embodiment of a RF electrode stylet according to this invention.

FIG. 4 is a cross-sectional view of a catheter with an extended stylet of one embodiment of this invention, and FIG. 5 is a cross-sectional enlarged view of the stylet tip shown in FIG. 4. In this embodiment, the catheter 48 is connected to a stylet guide housing 50 with a nose 52. The stylet 54 comprises a solid core needle 56 coaxially positioned within a tube 58, both of which are preferably constructed of a highly flexible, conductive metal such as nickel-titanium alloy, tempered steel, stainless steel, beryllium-copper alloy and the like. Nickel-titanium and similar highly flexible, shaped memory alloys are preferred. The needle 56 is axially or longitudinally moveable within the tube 58. The tube 58 is enclosed within a non-conductive, non-dielectric sleeve 60 which is longitudinally moveable along the tube. The guide housing 50 has a guide channel 61 which is curved to permit longitudinal advancement of the flexible stylet.

The sleeve 60 is connected to an annular cylinder 62 connected with a longitudinal thrust tube 64. Longitudinal movement of the thrust tube 64 causes a corresponding longitudinal movement of the sleeve 60 along the tube 58. The sleeve movement is used to vary and control the length of tube 58 and needle 56 exposed to surrounding tissue and control the amount of energy delivered to the target tissue. The material, insulating properties, dielectric properties and thickness of the sleeve 60 are selected to prevent heating energy delivery to tissue in contact therewith by shielding the tissue from the conductor. If the tissue is to be heated using radiofrequency current (300 to 750 kHz), the sleeve 60 must have sufficient thickness required to prevent both current flow and capacitance coupling with the tissue.

Figure 6:
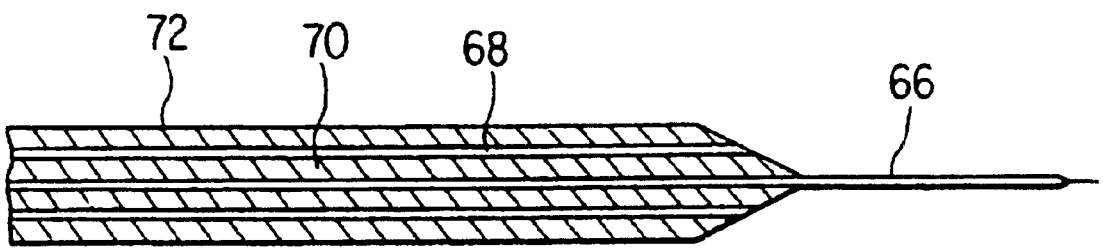
FIG. 6 is a cross-sectional representation of an embodiment of a microwave antenna stylet according to this invention.

FIG. 6 is a cross-sectional representation of an embodiment of a microwave antenna stylet according to this invention. This stylet comprises a coaxial central conductive needle wire 66 concentric with a surrounding conductive wire mesh or tube 68, the space therebetween being filled with a conventional dielectric solid 70. The conductive wire mesh or tube 68 is enclosed within an insulating sleeve or coating 72. After the stylet is advanced into tissue to be treated, electric power is delivered (900 to 2500 MHz), creating a electromagnetic microwave field of destructive energy in the tissue surrounding the needle antenna 66.

Figure 7:
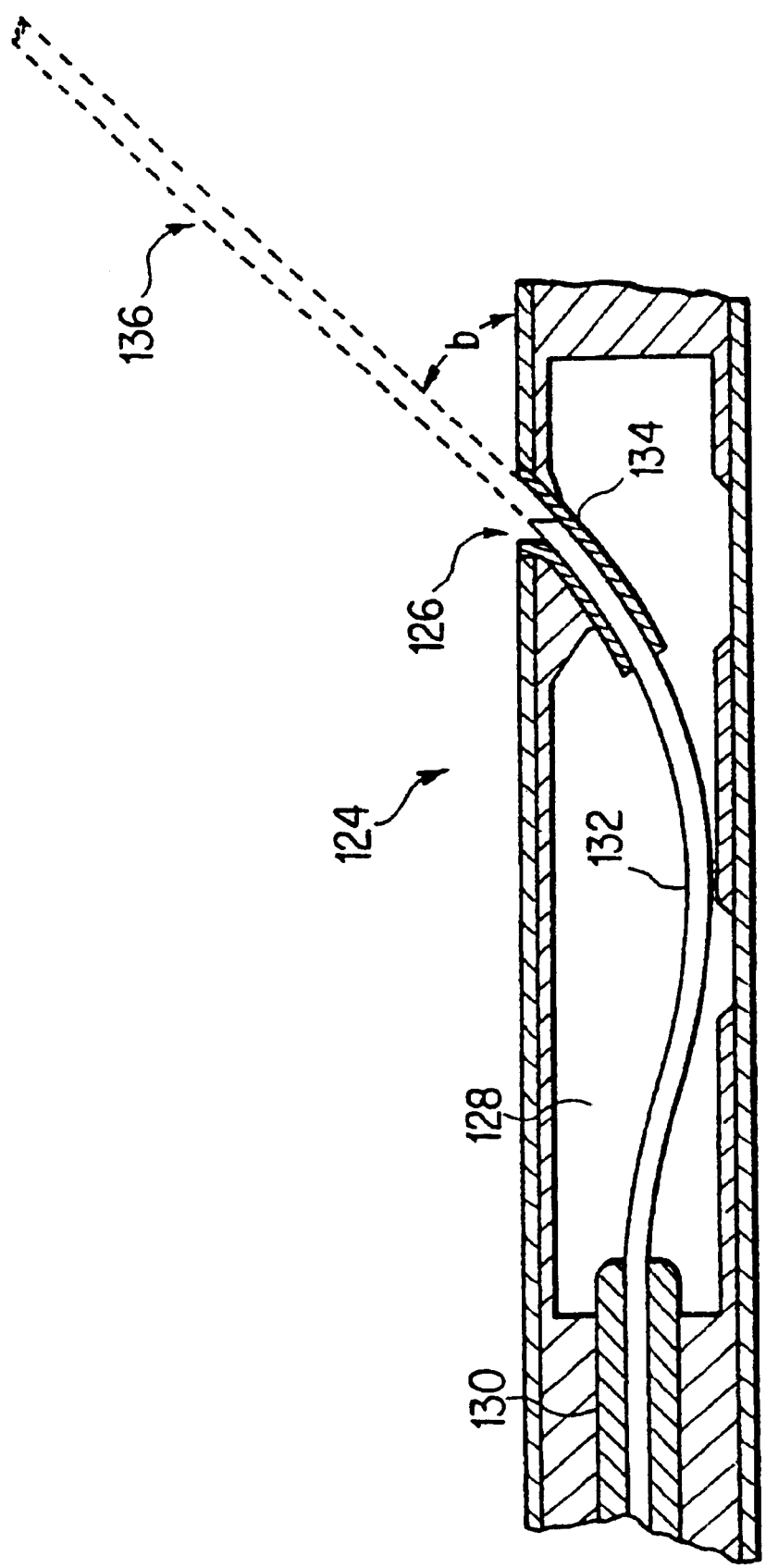
FIGS. 7 and 8 are cross-sectional representations of an embodiment of the catheter of this invention with a stylet guide system for adjusting the stylet guide angle.
Figure 8:
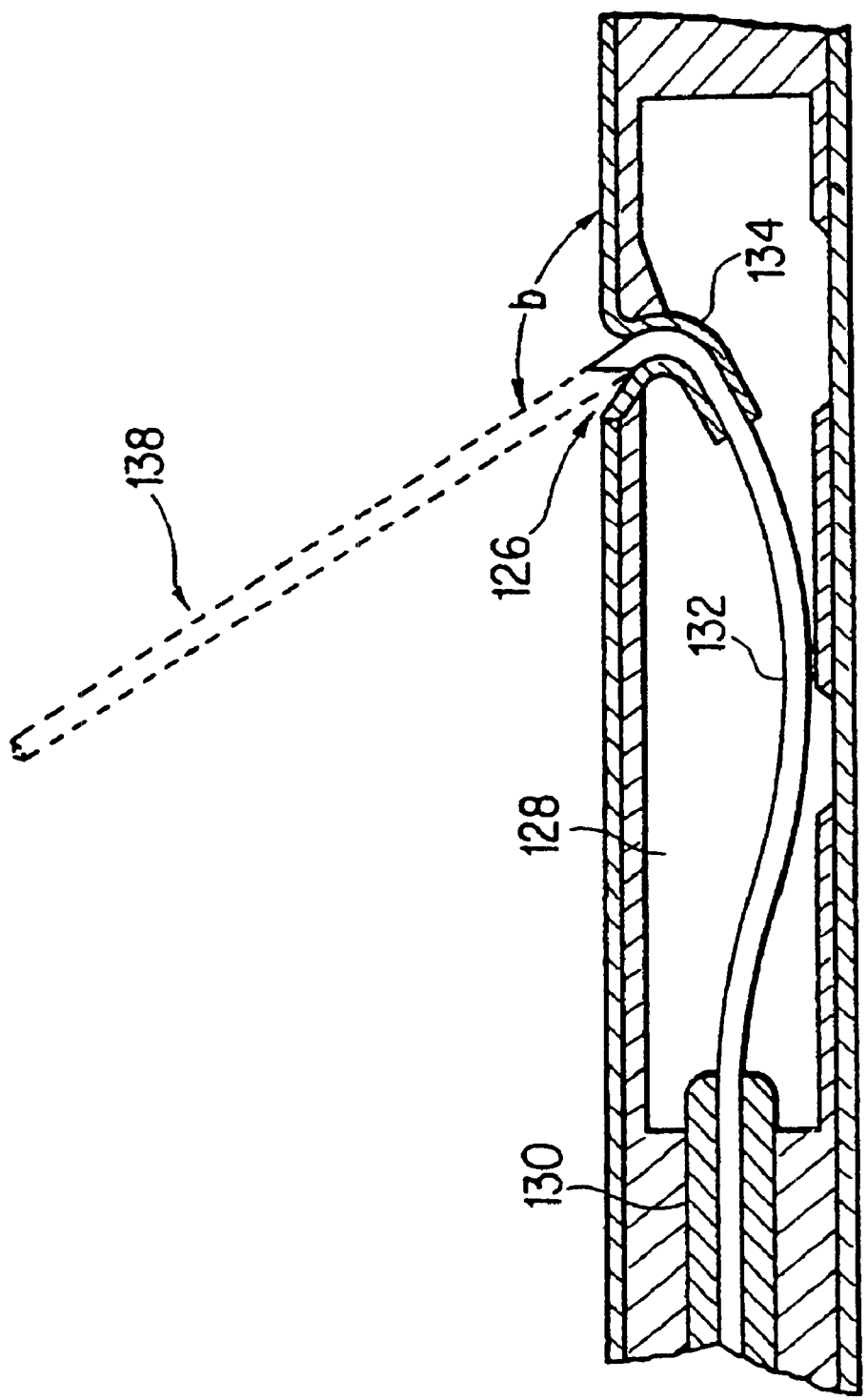

FIGS. 7 and 8 are cross-sectional, fragmentary representations of an embodiment of the catheter of this invention with a stylet guide system for adjusting the stylet guide angle. The stylet guide housing 124 has a stylet port 126. Within the guide housing 124, a stylet positioning block 128 is positioned for axial movement under the action of torque and thrust rod 130. The stylet positioning block 128 has a curved stylet lumen containing the stylet 132. optionally, a low friction, flexible guide tubing 134 extends from the positioning block 128 to the port 126. In the position shown in FIG. 7, the positioning block 128 is in a retracted position, orienting the stylet to extend at an acute angle "b" of approximately from about 20° and preferably 30° up to 90° with respect to the central axis of the guide housing. Advancement of the stylet 132 through the block 128, guide tubing 134 and port 126 directs the stylet into tissue along the dotted line path 136.

Advancement of the positioning block 128 as shown in FIG. 8 forces the stylet 132 through a curved path having a smaller diameter through guide tubing 134 to the port 126. The stylet 132 is then directed an obtuse angle which can be as high as about 160° with respect to the guide housing axis. Advancement of the stylet through the guide block 128, guide tubing 134 and port 126 in this configuration directs the stylet into tissue along the dotted line path 138.

As shown in FIG. 7 and 8, the angular projection of the stylet 132 can be oriented over a wide range of angles in a plane through the central axis of the stylet guide housing. It will be readily apparent that rotation of the torque and thrust rod 130 about its central axis will cause a corresponding rotation of the stylet guide housing and deflection of the stylet in directions outside of the axial plane. This combined with axial movement of the catheter to an optimum position in a duct and rotation of the catheter about its central axis yields an infinite variety of stylet orientation angles. A combination of these movements provides greater choices of stylet angles so that the stylet can be advanced into target tissue at any angle from the catheter.

Figure 9:
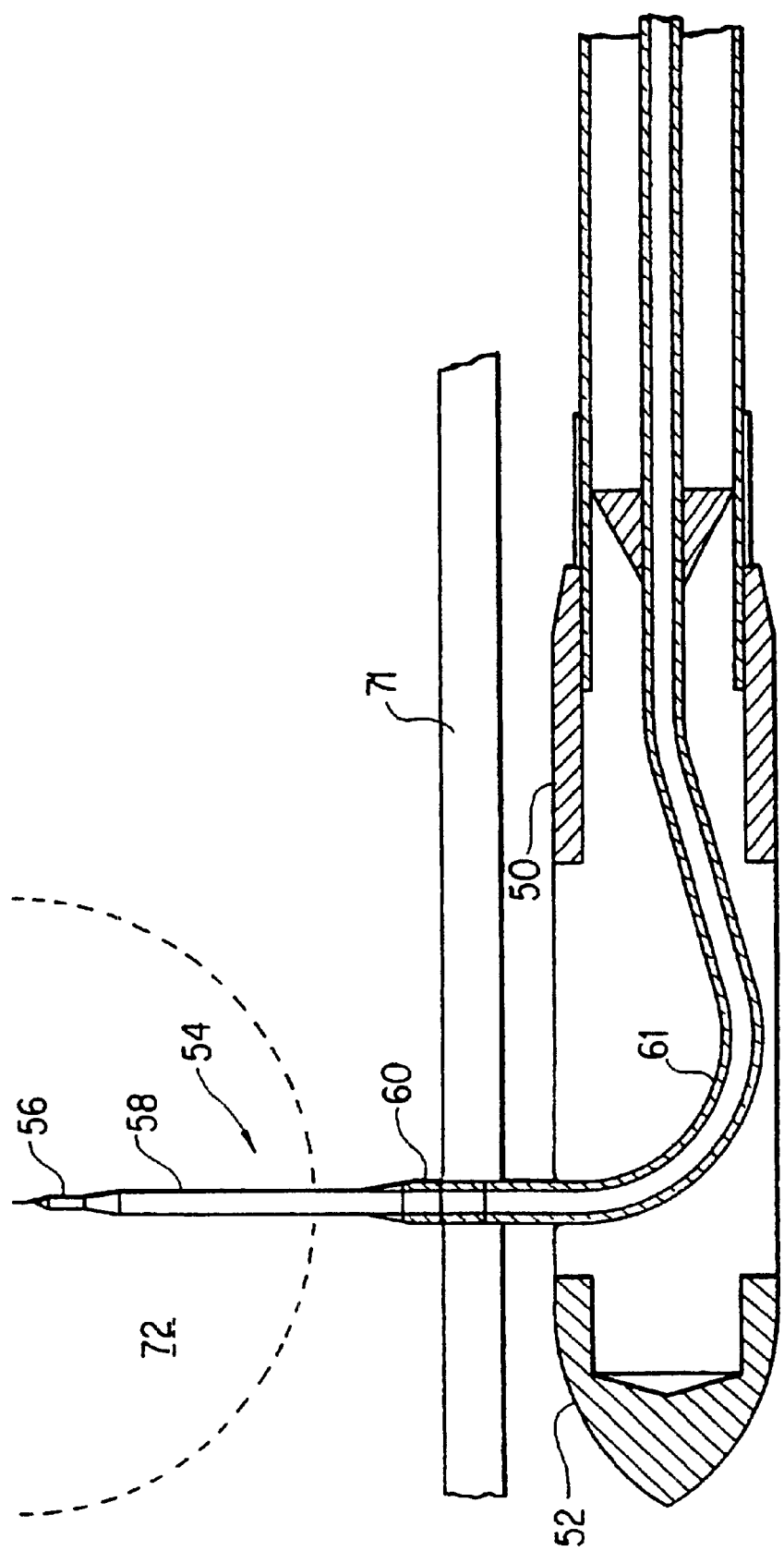
FIGS. 9 and 10 are detailed schematic cross-sectional views of a RF electrode stylet shown in FIG. 4 with a partially retracted sleeve positioned to treat tissue targeted for destruction while shielding intervening tissue from treatment according to the method of this invention.
Figure 10:
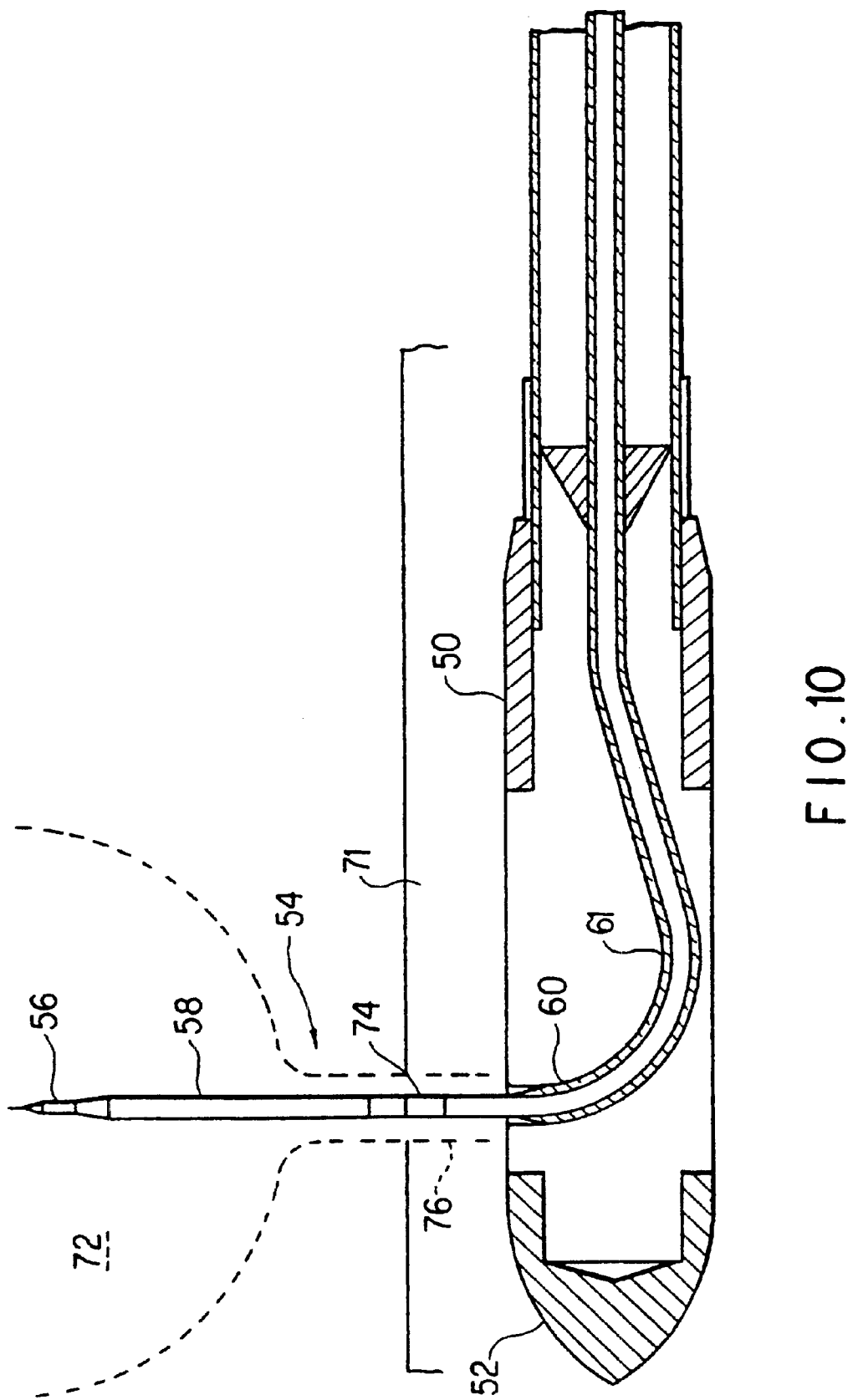

FIGS. 9 and 10 are detailed schematic cross-sectional views of a RF electrode stylet shown in FIG. 4 in use. After the catheter is positioned in the urethra, the stylet 54 is advanced from the stylet guide housing 50 through the prostatic urethra wall 71 to the target tissue 73 to be treated (outlined with a dotted line). Then, stylet sleeve 60 is retracted to the position shown in FIG. 9, exposing the portion of the RF electrode positioned in the target tissue 73. RF current is then directed from the electrode 56 and 58 through tissue 73 to conventional grounding plates (not shown). In selected instances, more directed ablation can be obtained by using one or more of the stylets as the indifferent electrode and another of the styles as the active electrode, thereby using only stylets to complete the dipole and not using a grounding plate. The RF treatment is continued until the cells in the target tissue 73 have been destroyed.

FIG. 10 is a detailed schematic cross-sectional view corresponding to FIG. 9 in an optional second step following the procedure described above. Following destruction of the cells in target tissue 73, the RF electrode sleeve 60 can be retracted along the stylet electrode 58 to the stylet guide housing 50, exposing a length of RF electrode 74 leading from the target tissue through prostatic urethra wall 71.

Sufficient RF current is then applied to cauterize the surface of the tissue 76 (shown by dotted lines) immediately in contact with the entire exposed surface of the electrode 58. For example, this can be achieved with a higher voltage and shorter duration treatment than is applied to destroy the cells of the target tissue. The stylet is then fully withdrawn into the housing 50, leaving a drainage duct leading from the area of the target tissue 73 to the prostatic urethra. This can provide drainage of the products of the treated target tissue 73 during the healing process.

The transurethral needle ablation (TUNA) process of this invention is a process whereby a physician in a unique procedure delivers radiofrequency or microwave energy to the hyperplastic tissues of the prostate which develop in men with the condition known as BPH, or Benign Prostatic Hyperplasia. This procedure is unique in that it is the first transurethral procedure which selectively provides the capability ability to limit the treatment to the constrictive tissue and spare the normal prostatic tissue. This procedure also minimizes the trauma sustained by the surrounding prostatic urethra, especially when compared to previously known procedures for relieving obstructive uropathy due to BPH. The procedure could possibly be carried out under local anesthesia only, depending upon the rate of energy delivery and degree of pain sensation experienced by the patient. When local anesthetic is adequate, the procedure can be performed in the physician's office. Local anesthetic could be delivered or applied in the form of a lubricant containing a topical anesthetic such as lidocaine mixed with K-Y jelly.

If substantial pain will be experienced by the patient, the patient must be sedated in addition to application of topical local anesthetic. This procedure can be provided on an outpatient basis and would require a short term (2–6 hour) observation. If the procedure and patient require greater pain control, then spinal anesthesia or a general anesthesia may be used for patients which qualify for their use. This would mandate that the procedure be carried out in the operating room, and would require a recovery room, and could possibly require in-patient care in certain circumstances. The previously known prostate resection (TURP) generally requires use of general or spinal anesthesia and in-patient hospital care following the treatment.

The BPH method of this invention can be carried out in the following manner, using a RF electrode stylet embodiment of this invention. A male patient is given the appropriate pre-procedure preparation which would usually require a fleets enema or bowel preparation. This would clear the rectal vault of stool in order to better place a rectal ultrasound probe, if used, and to assure better visualization.

Appropriate anesthetic, would then be administered. A conventional grounding plate is then placed in contact with the patient. The rectal probe would then be inserted to the level of the prostate in order to obtain an ultrasound image of the prostate. The procedure could be done without the use of rectal ultrasound, using only direct visualization at the discretion of the operator. The urethral catheter would then be inserted in a fashion similar to that used for inserting a Foley catheter. First the glans and the penile shaft would be bathed in betadine or other disinfectant. The rest of the groin adjacent areas are draped with sterile towels in the usual fashion. Then using aseptic or sterile technique, the shaft of the penis is grasped in one hand while the catheter is inserted into the urethral meatus and advanced until it has reached to desired position in the prostatic urethra. The catheter movement during its advancement through the urethra can be monitored directly with the ultrasound image. If direct visualization with fiber optics is used, the appropriate landmarks are located and identified, i.e., verumontanum and bladder neck, etc. If this has not been accomplished earlier, the various electrical and mechanical connections between the catheter and the control assembly are connected at this stage.

The RF electrode stylet is then deployed under direct vision or ultrasound imaging into a selected target tissue. This requires that the physician locate the target area to be treated, rotate, advance and/or retract the catheter as necessary to orient the stylet guide port toward the target area. The stylet, preferably completely enclosed in its insulating sleeve or sheath, punctures and penetrates the epithelial lining of the prostatic urethral, traveling through prostatic tissue to the target tissue, and penetrating the tissue to the desired depth. Local anesthetic can be infiltrated into the target tissue through the central lumen of the stylet as the stylet is advanced. The insulating sleeve is then retracted the amount required to expose a precise selected length of the RF electrode in the target tissue. This amount is selected to effect the degree and volume of tissue destruction desired, the volume increasing as the length of the exposed electrode increases. This volume is selected based on the size of the target tissue to be ablated and the relative position of the electrode stylet in the target tissue. The distance the sleeve is withdrawn can be measured external to the body using a conventional measuring devices such as a scale.

The electrode stylet is then energized from an RF energy source by closing a conventional switch. Preferably, the time and/or power levels are preset by the control unit. The RF energy is delivered to the target tissue for a preselected time, monitoring the advance of the destructive lesion by the rectal ultrasound image. Impedance is also monitored, and when or if it exceeds a preset value, the power supply can be reduced or terminated. The temperature of the catheter surface adjacent the urethral lining, the sleeve and even the exposed electrode can also be monitored using temperature sensors attached to these components to precisely control the volume of the lesion and prevent excessive heating of normal tissue.

After the target tissue destruction has proceeded to the desired stage, the physician has two options. The stylet electrode can be withdrawn into the catheter to facilitate quick healing and rapid sealing of the urethral puncture site. Alternatively, the physician can create a temporary physiological drainage capillary which would allow any fluid or debris accumulating in the ablated target tissue to drain into the urethra. This physiological drainage capillary can be created after target tissue destruction by withdrawing the insulating sleeve or sheath back into the urethral catheter as shown in FIG. 10. The conductive stylet is then energized to a level sufficient to "sear" or cauterize a small hollow channel through the tissue. This channel will eventually scar and fibrose, or it will seal and heal. The conductive stylet is then entirely withdrawn, and the catheter is slowly and carefully withdrawn from the urethra. The patient is then monitored and treated as appropriate for the type of anesthesia delivered and the condition of the patient.

Figure 11:
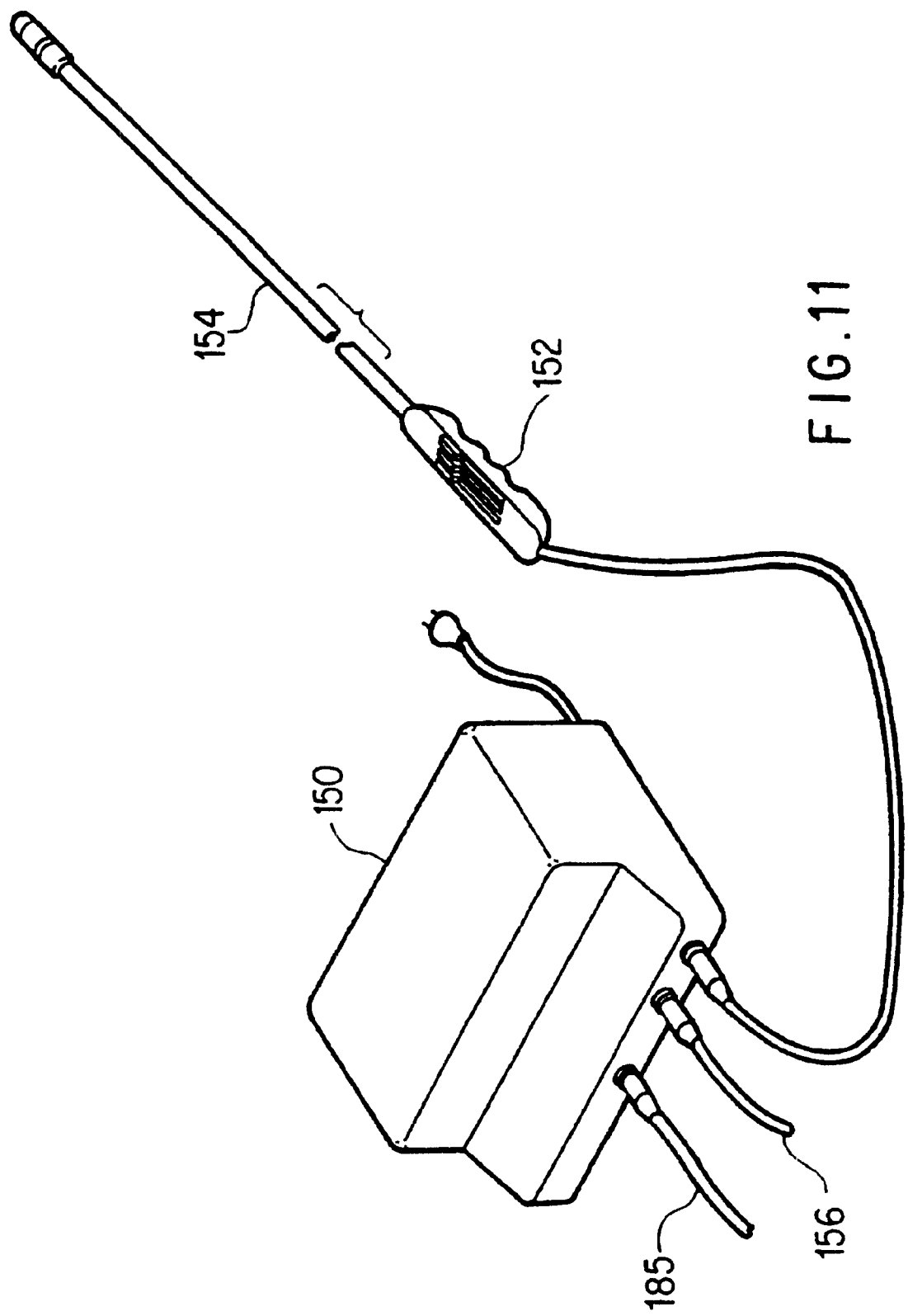
FIG. 11 is a schematic view of the assembly of control system, manual catheter control unit and catheter according to this invention.
Figure 12:
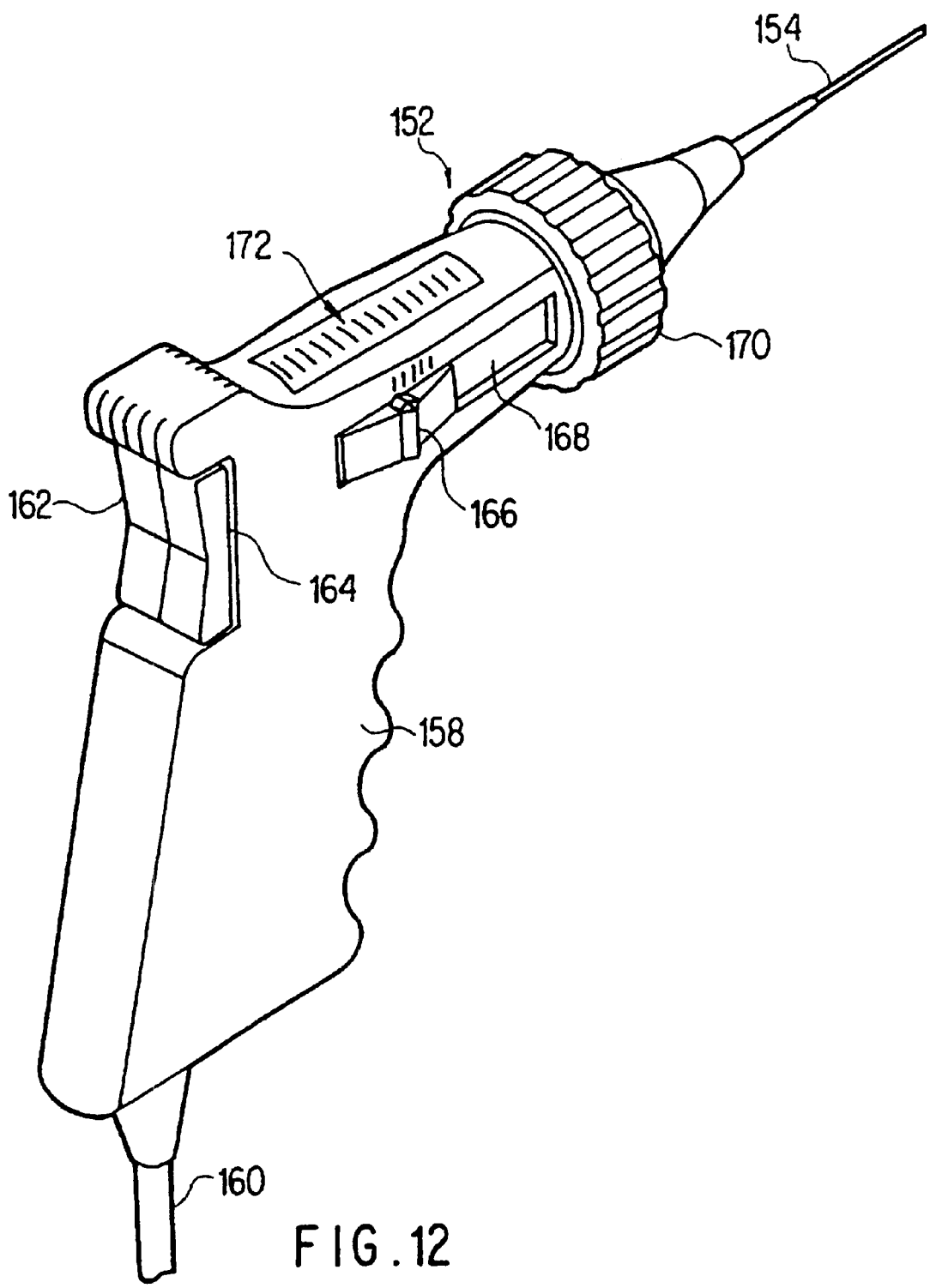
FIG. 12 is an isometric representation of an embodiment of a manual control system of the system of this invention.

FIG. 11 is a schematic view of the assembly of the control system 150, a manual catheter control unit 152, catheter 154, and power foot control 156. The power foot control functions can be accomplished by numerous other methods to include manual digital switches on control box 150 and by a trigger device on the catheter handle 152. The manual operation of the catheter assembly is controlled from a manual control unit shown in greater detail in FIG. 12, with the power control and temperature displays being provided in the control system 150 shown in greater detail in FIG. 13.

Figure 13:
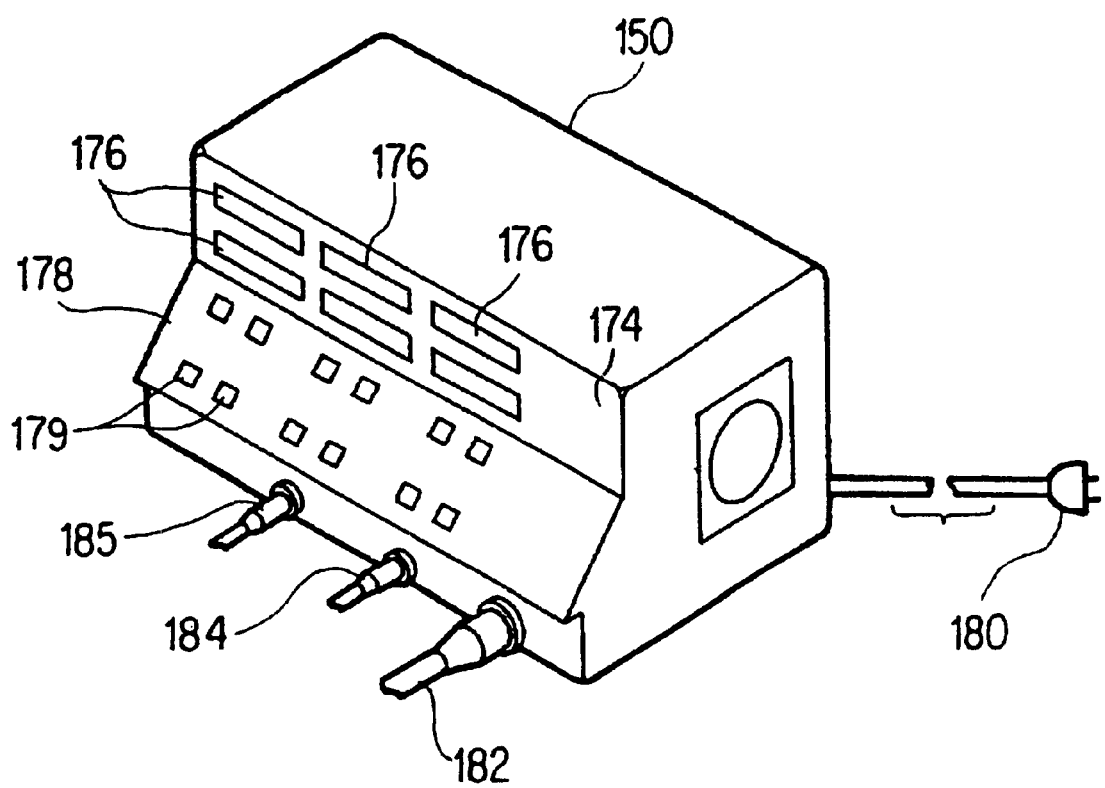
FIG. 13 is an isometric representation of an embodiment of a power and control console of the system of this invention.

FIG. 13 is an isometric representation of an embodiment of a manual control system of the system of this invention. The manual control 12 has a pistol grip 158 with a tube 160 leading to the console shown in FIG. 14. The tube 160 houses RF or microwave power supply cables, temperature sensors, ultrasound transducer power and signal delivery leads, balloon inflation fluid and vacuum lumens.

Rocker switches 162 and 164 provide control over the inflation or deflation of balloons 30 and 32 (FIGS. 1 and 2). Tab 166 sliding in groove 168 is connected to a stylet 62, advancing it into the a target tissue as the tab 166 is moved forward. Rotary dial 170 is attached to the catheter 154 and can be used to rotate the catheter for orientation of the stylet or stylets. Window 172 has graduations showing the percentage of balloon expansion.

FIG. 13 is an isometric representation of an embodiment of a power and control console 150 of the system of this invention. The housing of this console has a display panel 174 with digital readout displays 176 showing power to the stylet, antenna temperatures, tissue temperatures, impedance values, and other data, for example. The housing can support a sealed membrane switch panel 178 having system control buttons 179. Power cord 180 leads to a standard power outlet. Cable 182 leads to the manual catheter control unit 152 shown in FIG. 12. Cable 184 leads to a optional power foot control unit. Cable 185 leads to the.grounding patch for use in unipolar systems.

Figure 14:
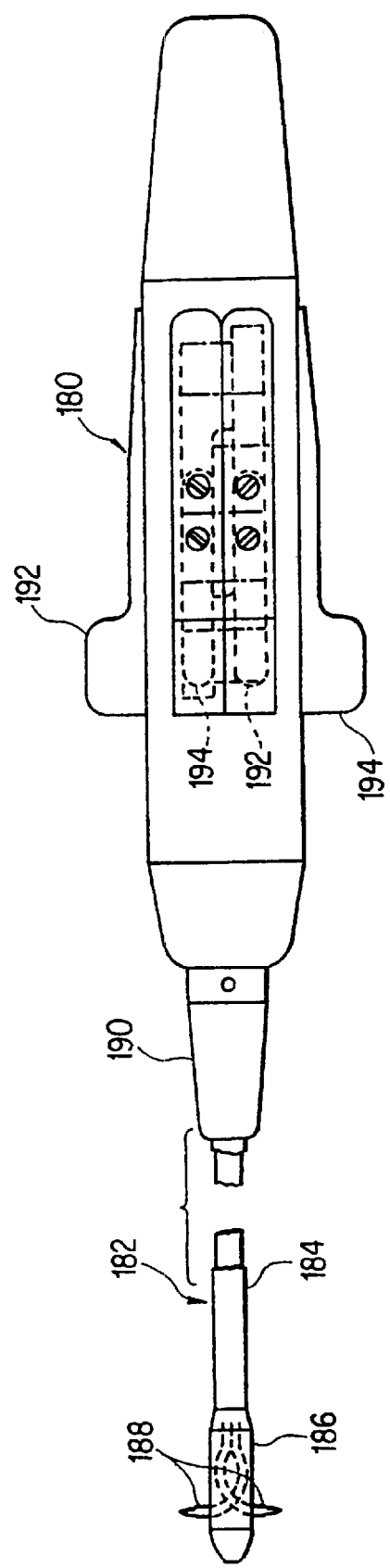
FIG. 14 is a view of an alternative four-probe embodiment of the device of this invention.

FIG. 14 is a view of an alternative four-probe embodiment of the device of this invention. The device comprises a handle portion 180 and a catheter portion 182. The catheter portion 180 includes an elongated catheter 184 having a distal catheter probe end 186. A plurality of stylets 188 extend outwardly from the probe end 186. The end 190 of the handle portion 180 is attached to the proximal end of the catheter 182, and manual control tabs 192 and 194 mounted thereon for sliding engagement with side walls of the handle portion. Using the handle 180 for control, the catheter is introduced into a body duct, vascular structure or canal such as the urethra, for example, and pushed up the duct to the treatment position, for example a position adjacent the prostate. Stylets 188 are individually and selectively passed outward from the distal end 190 through surrounding tissue to the target tissue to be treated by movement of respective manual control tab pairs 192 and 194. When the stylets are electrical conductors surrounded by moveable sleeves, the sleeves can be retracted from the end of the stylets by movement of manual control tabs 194 as described in greater detail hereinafter. Preferably, the proximal portion of the catheter 182 is preferably stiff to facilitate control during insertion in a body duct, while the distal portion is preferably flexible to allow the catheter to pass through curved duct portions.

Figure 15:
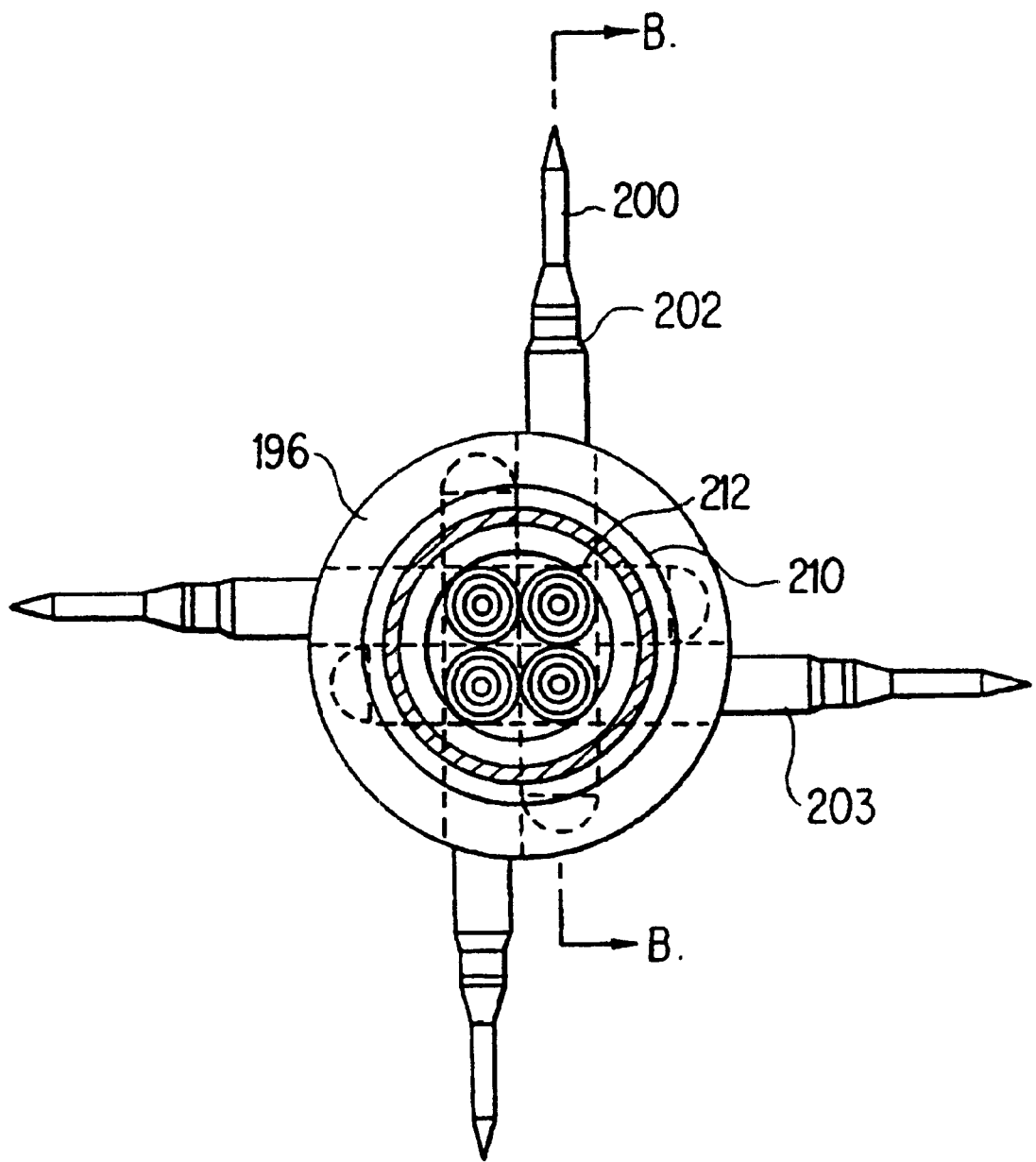
FIG. 15 is a side view of the distal probe end of the catheter shown in FIG. 14.
Figure 16:
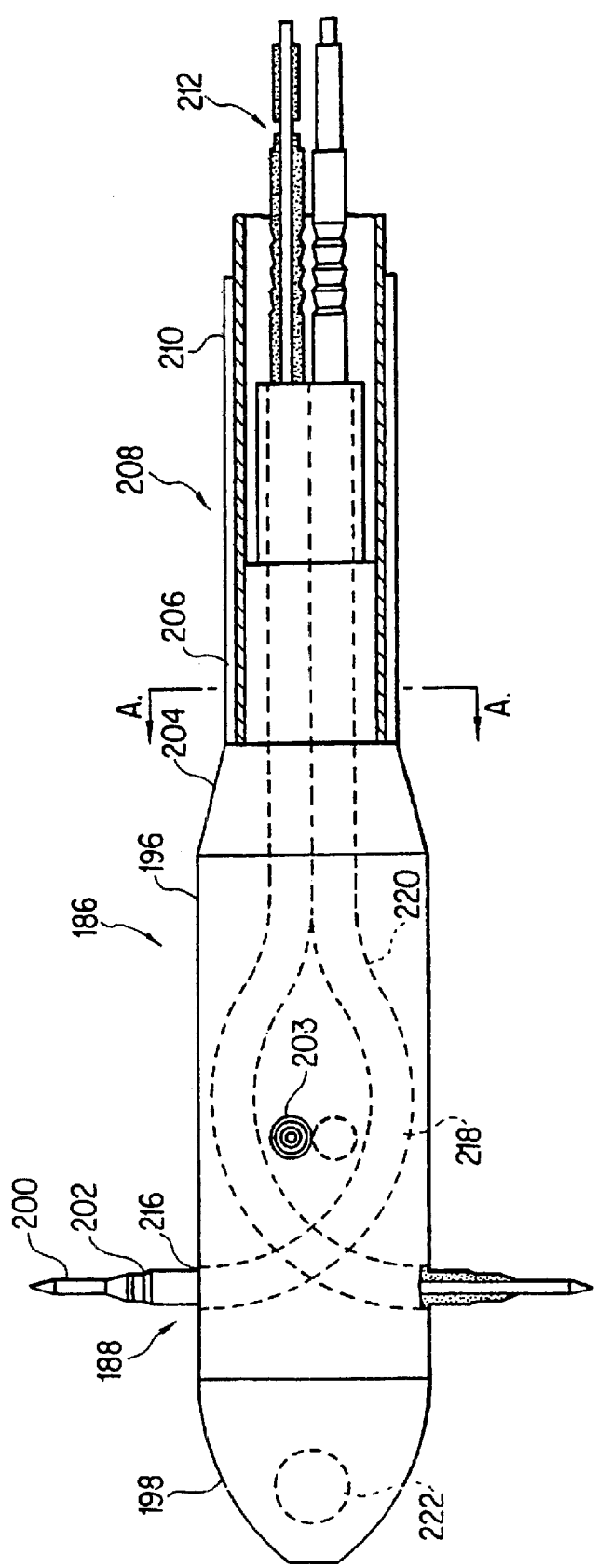
FIG. 16 is a cross-sectional end view of the probe end of the device shown in FIG. 15, taken along the line A—A.

FIG. 15 is a side partially sectioned view of the distal probe end of the catheter shown in FIG. 14 with stylets extended from the side ports, and FIG. 16 is a cross-sectional end view of the probe end of the device shown in FIG. 15, taken along the line A—A. The distal catheter tip 186 is a stylet guide housing having a lateral surface 196 which merges with a tapered tip portion 198. The stylets 188 extend outwardly from the lateral surface 196 and comprise an electrode 200 and moveable surrounding sleeve 202. The proximal portion 204 of the stylet guide is connected to the distal end 206 of the catheter stem 208. Further stylet ports such as the port from which stylet 203 extends are positioned at a greater distance from the tip 198 than ports 216. The embodiment shown in FIGS. 15 and 16 comprises two sets of stylets, each pair extending from ports in a common plane perpendicular to the catheter central axis. It will be readily apparent to a person skilled in the art that other stylet arrays such as a longitudinal array or a spiral array can also be used, and these variations are considered to be fully within the scope of this invention.

The catheter stem 208 includes an outer tubular housing 210 which encloses a plurality of stylets stems 212 disposed in a parallel relationship. As can be seen from FIG. 16, the individual stylets are directed outward in paths which have axes forming angles with each other. Oppositely disposed stylets can form an angle of up to 180° while in the configuration shown, the axis of adjacent stylets can form an angle of up to 90° for example.

Figure 17:
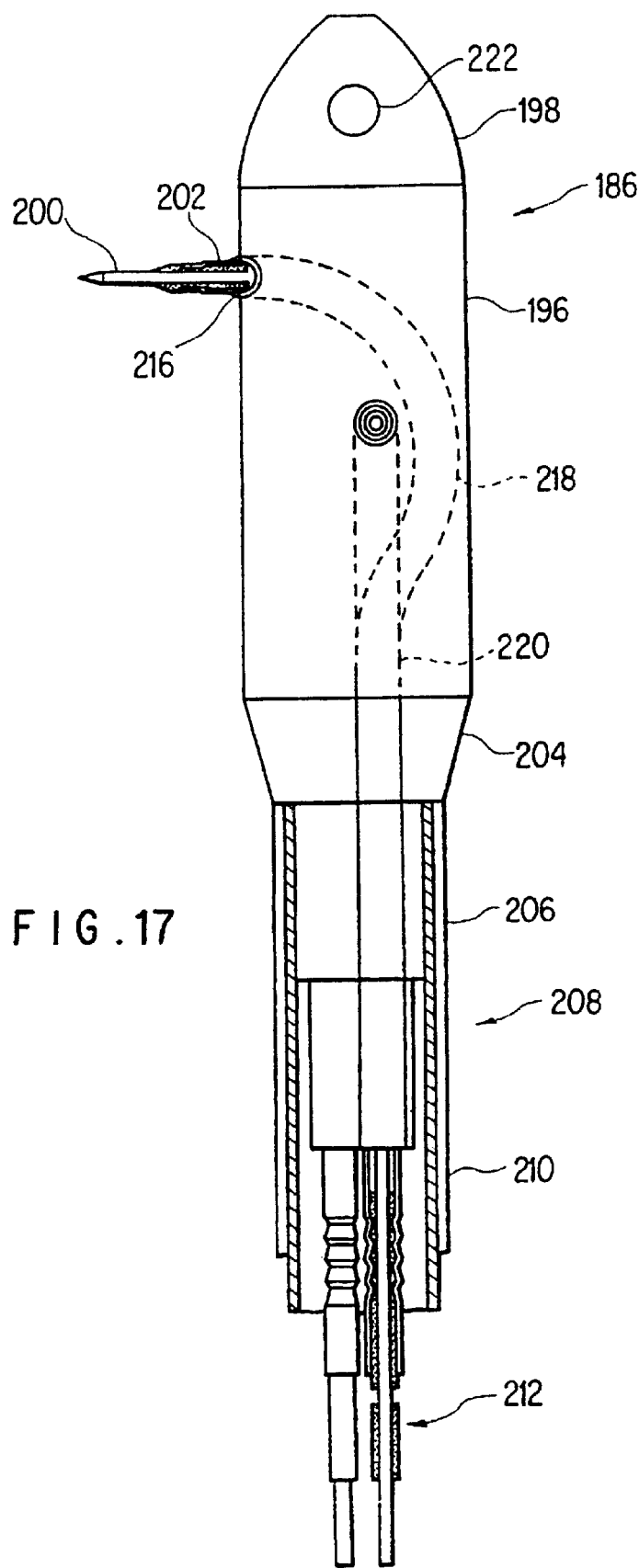
FIG. 17 is a partial cross-sectional view of the probe end of the device of this invention, taken along the B—B of FIG. 16.

FIG. 17 is a partial cross-sectional view of the probe end of the device of this invention, taken along the B—B of FIG. 16. The stylet is directed through a stylet guide means 214 in the distal catheter end 186 which leads from a path in the proximal catheter end 204 parallel with other stylet guides to a lateral orientation through stylet port 216. To facilitate longitudinal movement of the stylet through the guide path, the guide path preferably has a curved portion 218 extending to the port 216. The curved path optionally has a radius which is sufficient to deflect the deployed, extended stylet to the desired angle, that is, a radius of up to 0.5 cm, depending upon the diameter of the catheter. Optimally, the guide path also has a reverse curved portion 220 which extending from the axially parallel path in the proximal catheter end 214 outwardly away from the port 216 to the beginning of the curved path 218.

The distal tip 198 of the catheter can have a hollow space or bubble 222 which reflects ultrasound, permitting its easy identification with ultrasound generated by a rectal probe as shown in FIG. 1. Alternatively, a transponder can be mounted in the distal tip 198.

Figure 18:
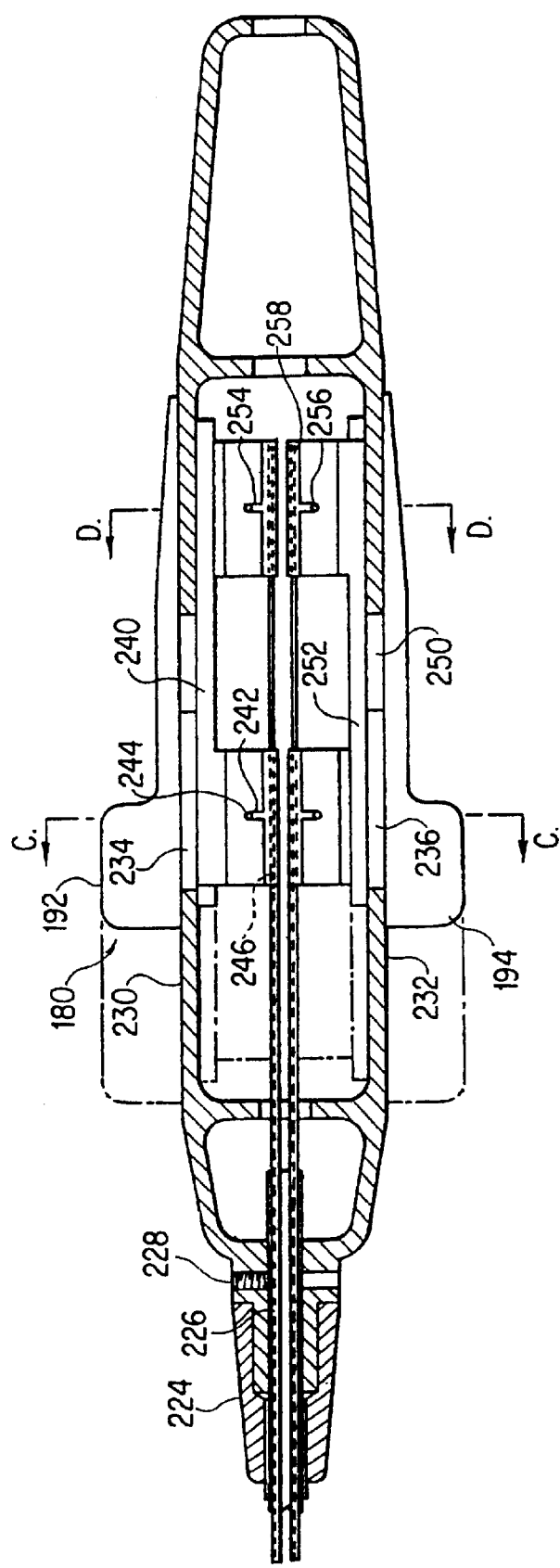
FIG. 18 is a cross-sectional view of the control end of the device shown in FIG. 14, taken along its central axis.

FIG. 18 is a cross-sectional view of the handle and control end of the device shown in FIG. 14, taken along its central axis. The control handle 180 is attached to the control end of the catheter stem 208. The handle 180 comprises a housing having a distal end forming an axial sleeve 224 enclosing the proximal end 226 of the catheter stem 208. The proximal end 226 is held in place by setscrew 228 extending through the sleeve 224. Manual engagement means 192 and 194 engage lateral handle housing walls 230 and 232, and are mounted for sliding engagement with respective slots 234 and 236 in the respective housing walls. They translate the manual motion into longitudinal motion of the stylet in the stylet guide means.

Figure 19:
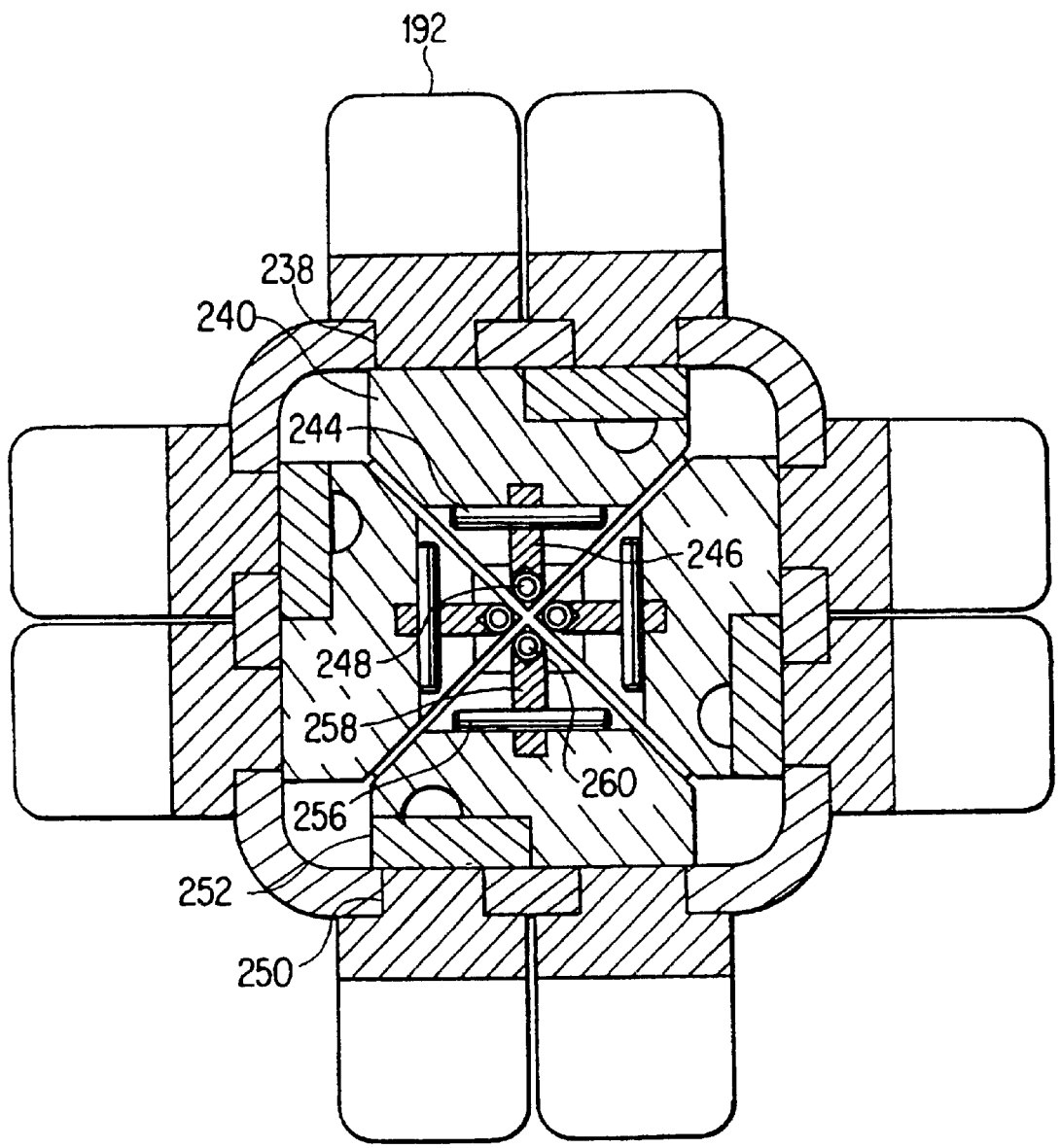
FIG. 19 is a cross-sectional view of the control end of the device shown in FIG. 18, taken along the line C—C.

FIG. 19 is a cross-sectional view of the control end of the device shown in FIG. 14, taken along the line C—C. Referring to both FIGS. 18 and 19, finger engaging sleeve movement tabs 192 are connected to connecting slide portion 238 extending through a respective longitudinal slot 234 and a inner portion 240 which forms a sliding engagement with the interior surface of the handle wall 230. Slot 242 in the connecting slide portion receives a pin 244 extending through a sleeve connector 246. Axial movement of the tab 192 thus effects an axial movement of corresponding sleeve 248 in the handle. Each side of the handle can have a pair of longitudinal, parallel slots to accommodate manual tabs for both sleeve and electric conductor.

Figure 20:
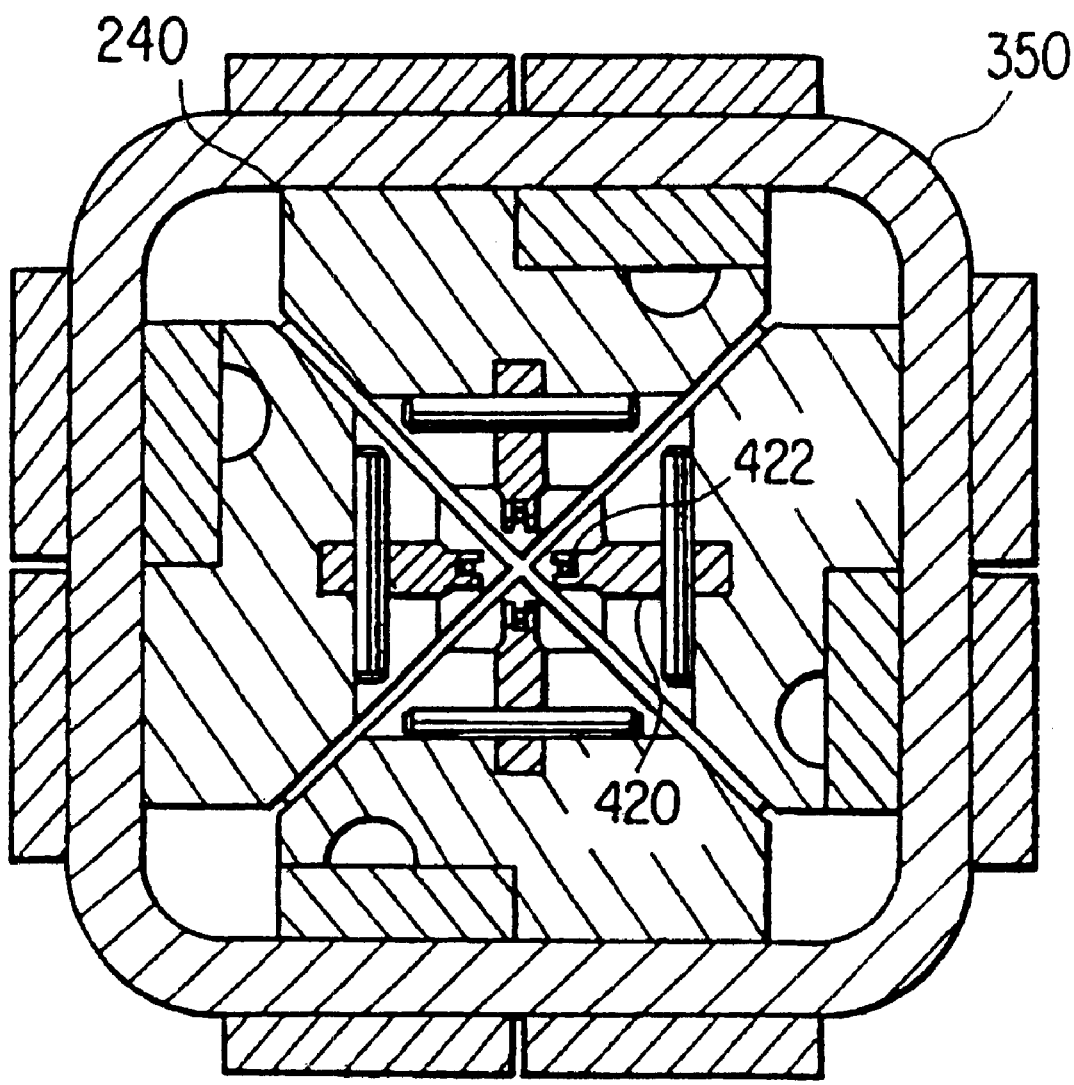
FIG. 20 is a cross-sectional view of the control end of the device shown in FIG. 18, taken along the line D—D.

FIG. 20 is a cross-sectional view of the control end of the device shown in FIG. 14, taken along the line D—D. Referring to FIGS. 18 and 20, finger engaging electrical conductor movement tab 194 is connected through a connecting slide portion 250 extending through a respective longitudinal slot 236 to a inner portion 252 which forms a sliding engagement with the interior surface of the handle wall 232. Slot 254 receives a pin 256 extending through a electrical conductor connector 258. Axial movement of the tab 194 thus effects an axial movement of the corresponding electrical conductor 260 in the handle.

Movement of adjacent tabs 192 and 194 advance the corresponding sleeve and electrical conductor together through the corresponding stylet guide, out the corresponding stylet port, and through intervening tissue to the target tissue to be ablated. Reverse movement of the sleeve tab 192 then retracts the sleeve to expose a selected area of the electrical conductor surface in the tissue, preparatory to ablation.

Figure 29:
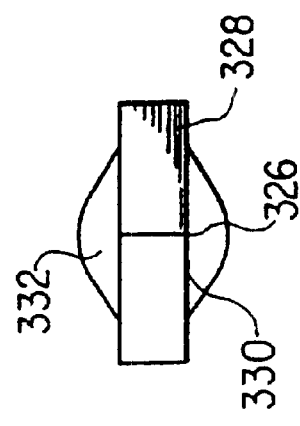
FIG. 29 is an end view of the electrode tip shown in FIG. 28.

FIG. 21 is a side view of the non-conductive sleeve connector of the embodiment show in FIGS. 18 and 29, and FIG. 22 is a cross-sectional view of the non-conductive sleeve connector shown in FIG. 21, taken along the line E—E. connecting pin 244 extends through a hole in the sleeve connector 246. An axial edge of the sleeve connector 246 is connected to the proximal end portion 248 of the sleeve.

FIG. 23 is a side view of the electrical conductor connector of the embodiment show in FIGS. 18 and 20, and FIG. 24 is a cross-sectional view of the electrical conductor connector shown in FIG. 23, taken along the line F—F. Connecting pin 256 extends through a hole in the electrical conductor connector 258. An axial edge of the electrical conductor connector 258 is connected to the proximal end portion 260 of the electrical conductor.

FIG. 25 is a cross-sectional view of the distal end of the non-conductive sleeve shown in FIGS. 16–18, taken along its central axis. The non-conductive sleeve 202 comprises a tapered leading tip 262 and a rigid proximal portion 264. A flexible portion 266 extends between the leading tip 262 to the rigid proximal portion 264. The flexible portion 266 can be any flexible configuration such as a spiral coil, wire braid, stainless steel tube, or any other flexible construction which yields a catheter which has the required flexibility and torque strength. If the flexible portion 266 and the rigid proximal portion 264 are made of a conductive materials such as metal, they can be covered with an insulating sleeve 268. The annular ridges 270 in the rigid proximal portion and the flange 272 in the tip engage the sleeve 268, securing the sleeve in place. The inner lumen 274 of the non-conductive sleeve 202 receives the electrical connector 200. A temperature sensor such a thermistor 271 can be mounted on the tip to provide local temperature information. An ultrasound transponder 273 can also be mounted on the tip to provide a signal useful for precise positioning of the stylet tip in a tissue to be ablated.

Figure 26:
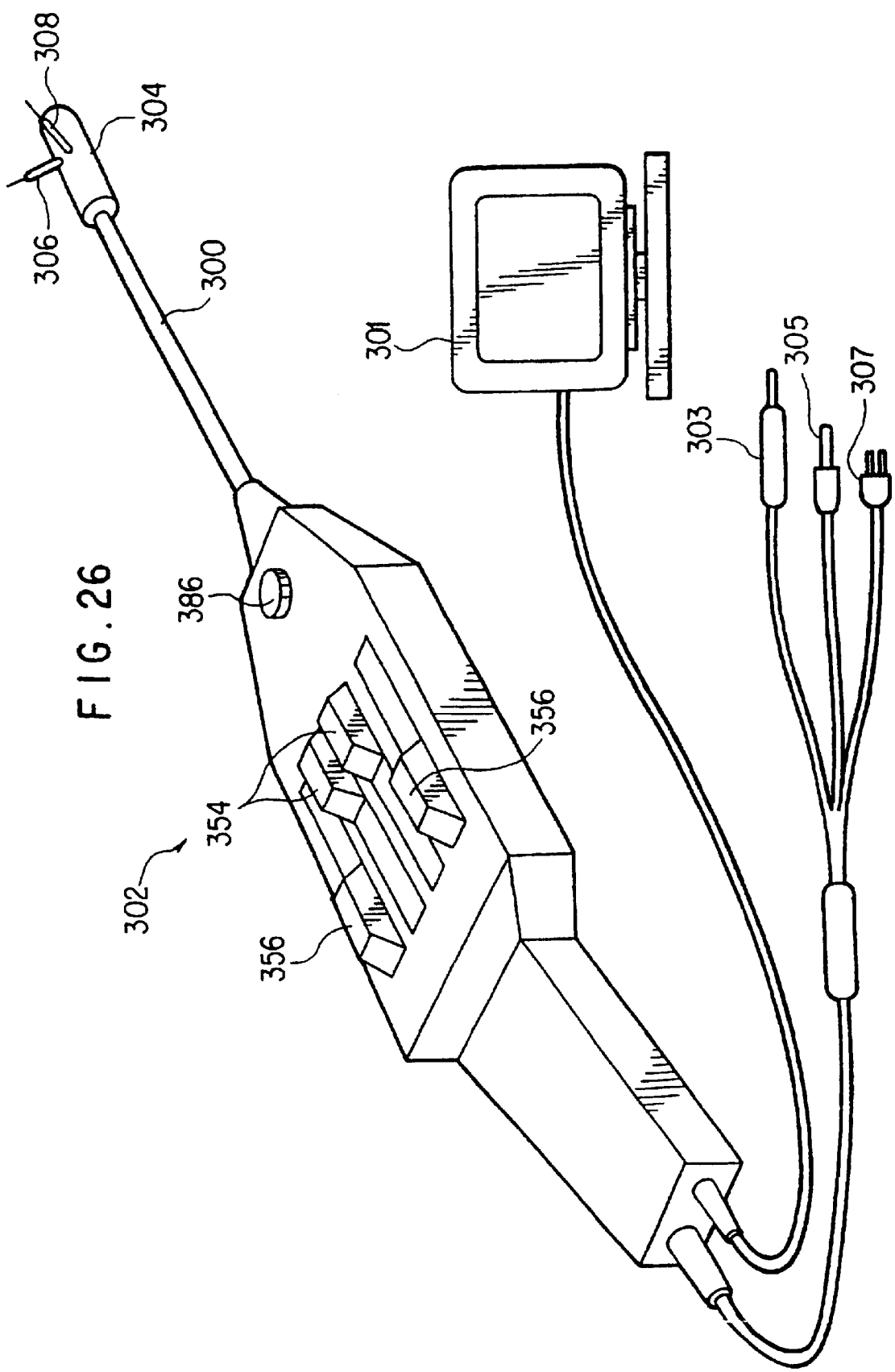
FIG. 26 is a top view of a two stylet alternative embodiment of an RF ablation catheter of this invention.

FIG. 26 is a top view of a two stylet preferred embodiment of an RF ablation catheter of this invention. The flexible catheter 300, attached to handle 302, has a terminal stylet guide 304 with two stylets 306 and 308. The handle has stylet sleeve tabs 356 and electrode tabs 354 as will be described in greater detail hereinafter. The handle is also connected to a visual monitor 301 and RF power connector 303, transponder connector 305 and thermocouple connector 307. The portions of the catheter 300 leading from the handle 302 to the stylet guide tip 304 can optionally has a graduated stiffness. For example, the catheter can be designed to be more stiff near the handle and more flexible near the tip, or any other stiffness profiles. The catheter can be constructed of an inner slotted stainless steel tube with outer flexible sleeve such as is described in copending application Ser. No. 790,648 filed Aug. 11, 1991 (corresponding to published Australian patent application Serial No. 9210858), the entire contents of which are incorporated herein by reference. It can also be made of coiled or braided wire to which an outer sleeve is bonded.

Figure 28:
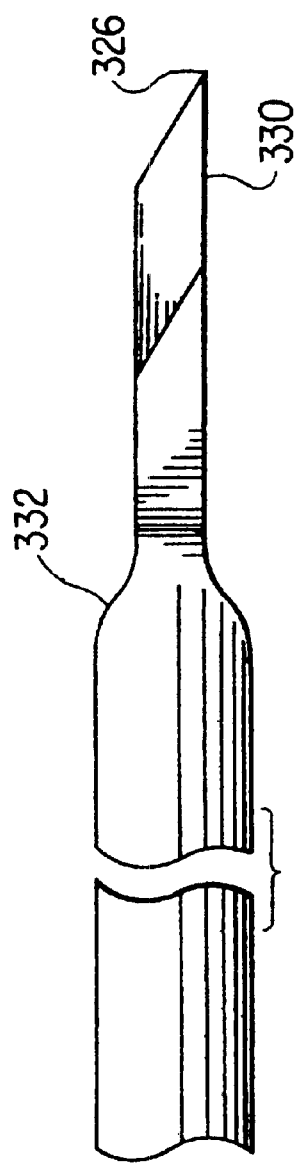
FIG. 28 is a side view of the single grind electrode tip shown in FIG. 27.
Figure 27:
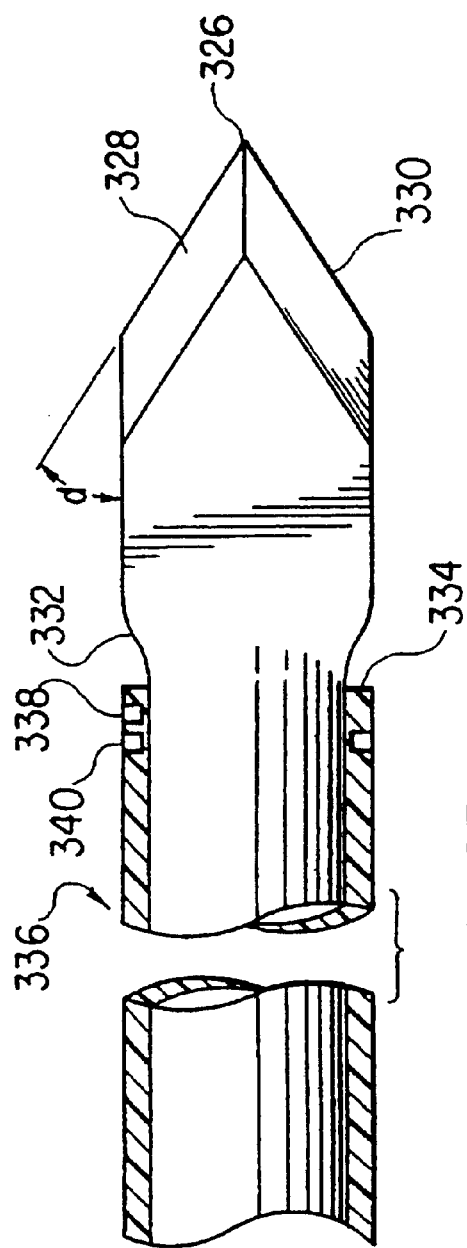
FIG. 27 is a top view of one embodiment of a stylet tip of this invention.

FIG. 27 is a top view of the stylet tip of the embodiment shown in FIG. 26, FIG. 28 is a side view of the single grind electrode tip shown in FIG. 27, and FIG. 29 is an end view of the electrode tip shown in FIG. 28. In this embodiment, the sharpened tip 326 and leading cutting edges 328 and 330 are formed by grinding one surface of the tip, the cutting edges forming an angle, "d", of from 15° to 45° and preferably from 25° to 35° with a line parallel with the central axis of the tip. The proximal surface of the tip forms a shoulder 332 which the leading or distal edge 334 of the sleeve 336 abuts, preventing movement of the sleeve 336 over the sharpened tip. The sleeve 336 can also support temperature sensors such as a thermistor 338 and a ultrasound transponder 340.

Figures 30, 31:
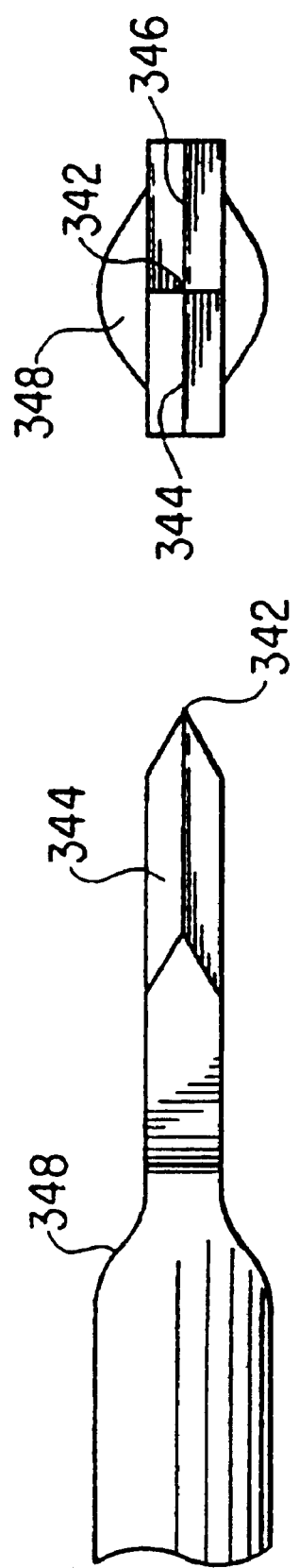
FIG. 30 is a side view of an alternative double grind electrode tip.
FIG. 31 is an end view of the electrode tip shown in FIG. 30.

FIG. 30 is a side view of an alternative double grind electrode tip, and FIG. 31 is an end view of the electrode tip shown in FIG. 30. In this embodiment, the sharpened tip 342 and leading cutting edges 344 and 346 are formed by grinding both surfaces of the tip. The proximal surface of the tip forms a shoulder 348 which the leading or distal edge of a sleeve (not shown) abuts, preventing movement of the sleeve over the sharpened tip. The forward cutting edges of this embodiment make little if any contact with the inner surface of the stylet guide in the catheter tip, preventing dulling of the cutting edge.

Figure 32:
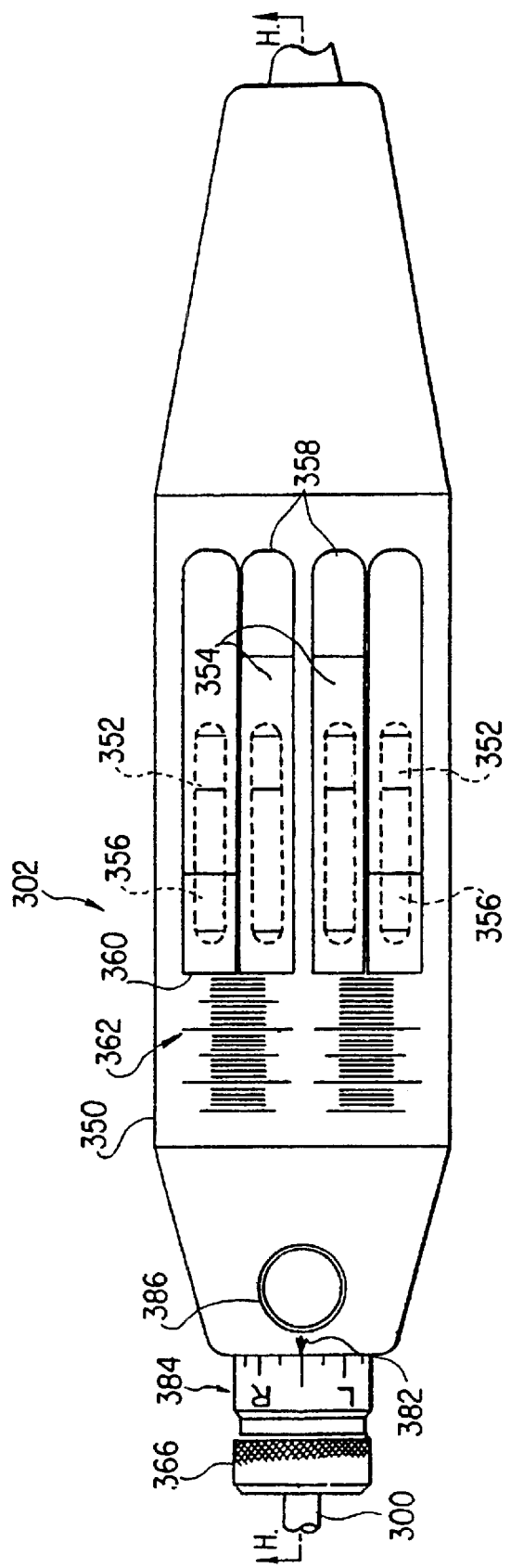
FIG. 32 is a top view of the handle portion of the ablation catheter of FIG. 26.

FIG. 32 is a top view of the handle portion of the ablation catheter of FIG. 26. The handle 302 has an upper housing plate 350 upon which stylet sleeve positioning slides 352 and electrode positioning slides 354 with manual tabs 356 and 358 are mounted for sliding movement in the direction of the central axis of the housing. The position of the leading edges 360 of the slides relative to the graduated markings 362 on the housing plate surface are used to determine the distance the sleeve and stylet have been advanced from the stylet guide toward tissue to be treated.

Figure 33:
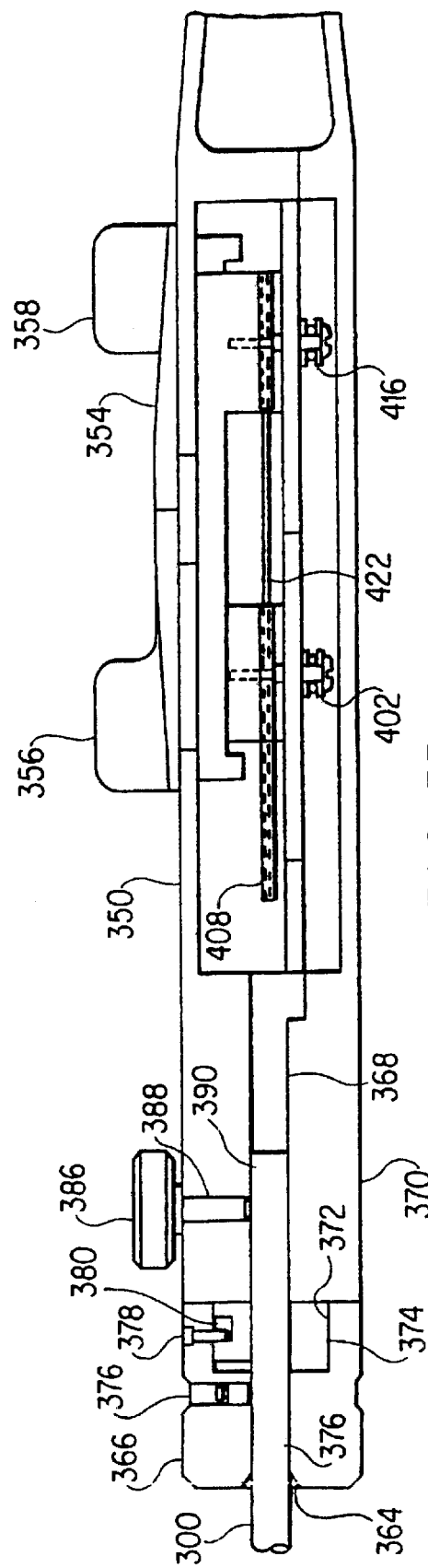
FIG. 33 is a side view of the handle portion shown in FIG. 32 taken along the line H—H with the bottom cover plate partially removed.

FIG. 33 is a side view of the handle portion shown in FIG. 32 taken along the line H—H with the bottom housing cover plate partially removed. The proximal end of the catheter 300 passes through a cylindrical hole 364 in the cylindrical knurled knob 366 and cylindrical receptor 368 formed by the opposed hemicylindrical surfaces in the distal ends of the upper housing plate 350 and lower housing plate 370. The proximal end of the knurled knob 366 has a cylindrical receptor 372 which forms a sliding fit with a cylindrical projection 374 formed by the distal ends of the housing plates 350 and 370. Setscrew 376 secures the knob 366 to the catheter 300 so they rotate together as a unit. Pin 378 extends through the knob 366 into an annular groove 380, allowing rotation but preventing axial movement of the knob 366 relative to the cylinder 374. The angular position of the knob 366 relative to the housing plate 350 is shown by the position of the arrow 382 relative to the graduations 384 on the knob (FIG. 32). Knurled knob 386 treadingly engages hole 388 in the housing plate 350. When the catheter knob 366 has been turned to rotate the catheter 300 (and the stylet guide on its end) to a desired stylet orientation, advancement of the knob 386 against the catheter surface 390 secures its angular position. The stylets are then advanced through surrounding tissue to the depth desired, as indicated by graduations 362.

Figure 34:
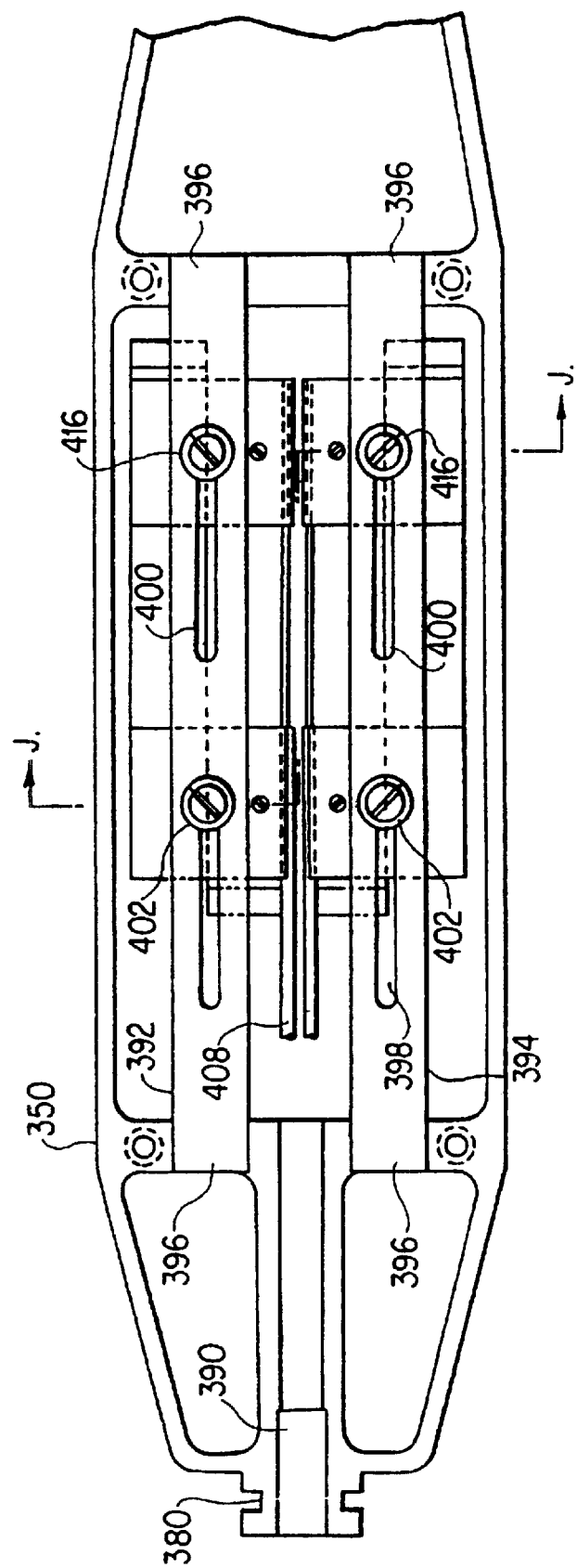
FIG. 34 is a bottom view of the handle portion shown in FIG. 32 with the bottom cover plate removed.
Figure 35:
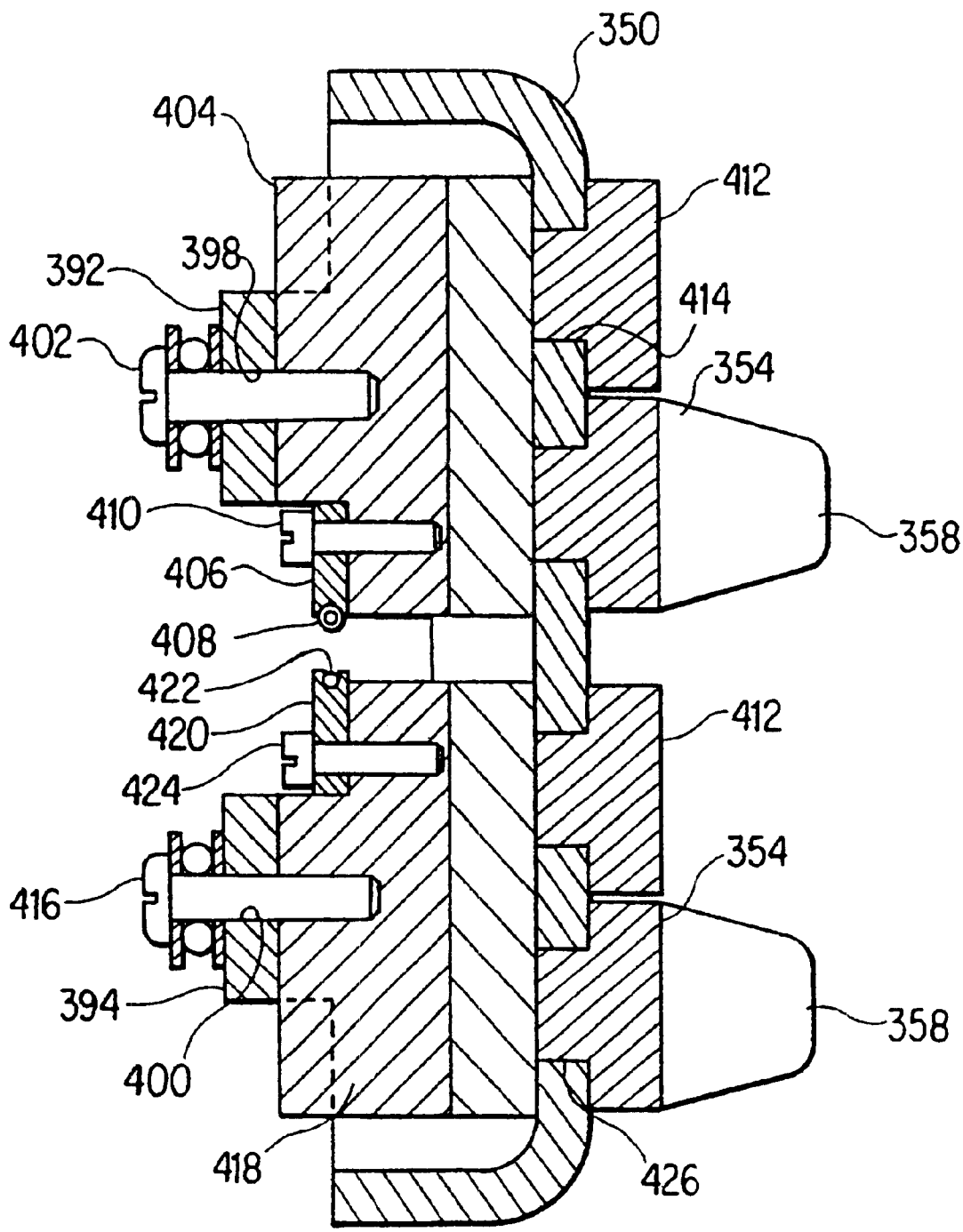
FIG. 35 is a cross-sectional view of the handle portion taken along the line J—J in FIG. 34.

FIG. 34 is a bottom view of the handle portion shown in FIG. 32 with the catheter, distal knob and bottom cover plate removed, and FIG. 35 is a cross-sectional view of the handle portion taken along the line J—J in FIG. 34. Stylet movement guide plates 392 and 394 are securely mounted in terminal end receptors 396 in the inner surfaces of upper housing plate 350. Each of the guide plates 392 and 394 has a sleeve guide slot 398 and a electrode guide slot 400 therein. Screws 402 extend through sleeve guide slots 400 and threadingly engage the sleeve guide blocks 404. Axial movement of the screws 402 and guide blocks 404 attached thereto is limited by the length of the slots 398. Sleeve connector 406 attached to stylet sleeve 408 is secured to the guide block 404 by screw 410. Slide plate 412 mounted for sliding movement in a slot 414 in the housing plate 350 is secured to guide block 404. Screws 416 extend through sleeve guide slots 400 and threadingly engage the electrode guide blocks 418. Axial movement of the screws 416 and guide blocks 418 attached thereto is limited by the length of the slots 400. Electrode connector 420 attached to stylet electrode 422 is secured to the guide block 418 by screw 424. Slide plate 354 mounted for sliding movement in a slot 426 in the housing plate 350 is secured to guide block 418.

Figure 38:
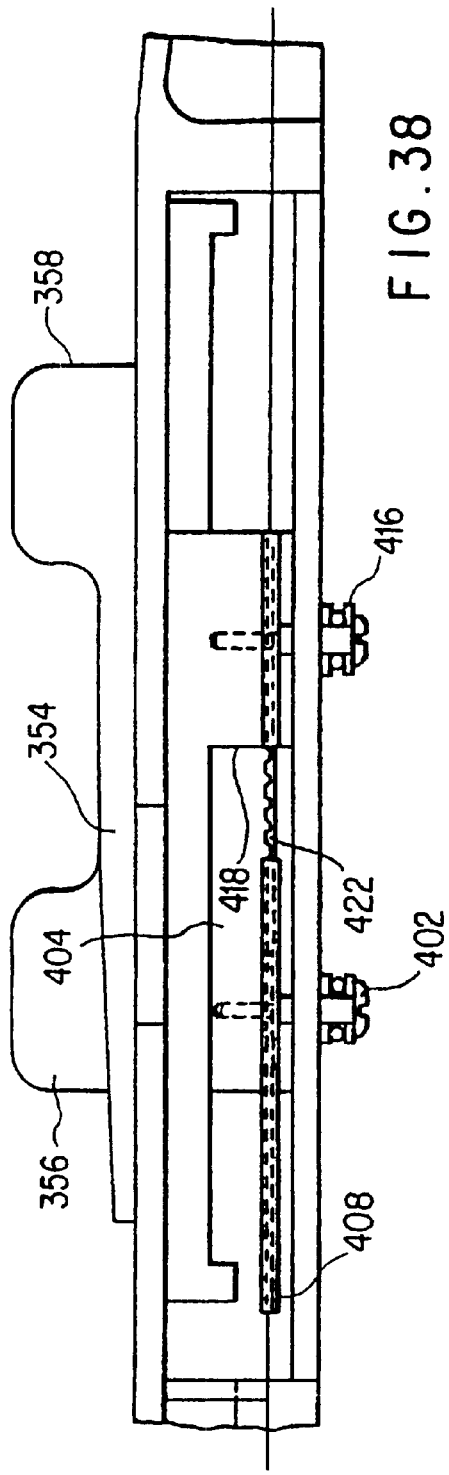
FIG. 38 is a cross-sectional view of the central portion of the handle portion shown in FIG. 33 with the stylet in an extended position and the sleeve partially retracted therefrom.

FIG. 36 is a cross-section view of the central portion of the handle portion shown in FIG. 33 in the stylet and sleeve retracted position (corresponding to the positions in FIG. 32). FIG. 37 is a cross-sectional view with the stylet and sleeve in an extended position, and FIG. 38 is a cross-sectional with the stylet in an extended position and the sleeve partially retracted therefrom. The stylets are extended after the catheter is inserted to place the stylet guides in a position laterally adjacent the target tissue to be treated and the catheter has been rotated to orient the stylet guide outlets in the direction of the target tissue. The stylets are extended through intervening tissue to the target tissue by moving the manual tabs 356 and 358 toward the distal end of the handle as shown in FIG. 37. This effects simultaneous movement of the stylet sleeve 408 and electrode 422. After the extension has proceeded to the extent required to place the tip of the electrode 422 in the target tissue, the sleeve 408 is retracted to the position shown in FIG. 38 by moving the manual tab 358 in the proximal direction to the extent required to expose the desired portion of the electrode as indicated by graduations 362 (FIG. 32). The RF current is then applied to the electrodes until the desired ablation has been achieved. With this embodiment, two stylets can be extended, sleeves retracted, and the ablation achieved either concurrently or sequentially.

Figure 39:
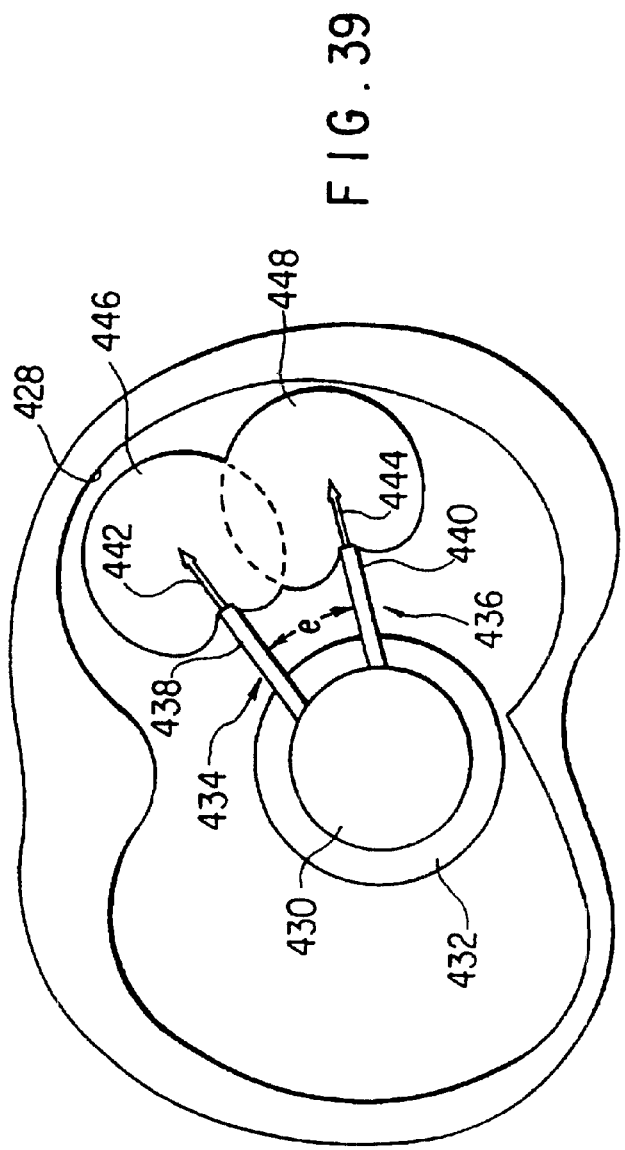
FIG. 39 is a schematic view of a deployment of two stylets in a prostate showing stylet orientation for overlapping ablation zone method of this invention.

FIG. 39 is a schematic view of a deployment of two stylets in a prostate showing stylet orientation for overlapping ablation zone method of this invention. For purposes of illustration but not by way of limitation, the prostate has been selected for this explanation, and application of this method and assembly to other areas of the body are intended to be included.

The tissues to be treated for the treatment of BPH are located in the transition zone 428 of the prostate. A catheter of this invention 430 has been inserted up the urethra 432 to a position adjacent the prostate. Two stylets 434 and 436 have been passed through the urethra wall 432 and surrounding tissue into the target tissue, and the non-conducting sleeves 438 and 440 have been retracted to expose a portion of the respective electrical conductors 442 and 444 at the end of each stylet. The angle between the axes of the stylets in this embodiment, "e", is less than 180°, preferably less than 110°. For most overlapping ablations, angles of 15° to 90°, and more usually from 20° to 70° are most practical. A Grounding plate (not shown) is placed on the body exterior.

When electrodes 442 and 444 are supplied with RF current, the circuit from the electrodes to a grounding plate is closed. The current density flowing through the tissue passes through the target tissue to be treated, creating lesions having the approximate cross-sectional shape of overlapping zones 446 and 448. The current density rapidly decreases as a function of distance, limiting the size of the lesions. In this manner, lesions can be caused to overlap to form a larger lesion, increasing the efficiency of the treatment. It will be readily apparent that these processes can be carried out concurrently, as described, or sequentially, and these variations are intended to be included in this invention.

Although preferred embodiments of the subject invention have been described in some detail, it is understood that obvious variations can be made without departing from the spirit and the scope of the invention as defined by the appended claims.

We claim:

1. A retractable RF electrode assembly for ablating and measuring the impedance of a body tissue portion, comprising:
    a) a first RF electrode having a distal end and a proximal end, said first RF electrode being disposed within an insulating sheath;
    b) elongated guide means encasing said first RF electrode and said insulating sheath, for guiding said first RF electrode into a predetermined angle value with respect to a longitudinal axis of said elongated guide means;
    c) electrode movement mechanism means, attached to said proximal end of said first RF electrode, for moving said first RF electrode within said guide means, said distal end of said first RF electrode being extendable beyond an open end of said guide means up to a predetermined length value and engagable with and insertable into said body tissue portion;
    d) energy source means, in electrical communication with said proximal end of said first RF electrode, for transmitting energy into said distal end of said first RF electrode when it is extended beyond said guide means and into said body tissue portion so as to ablate said body tissue portion; and
    e) tissue impedance measurement means, in electrical communication with said proximal end of said first RF electrode, for measuring an impedance associated with said body tissue portion engaged with said distal end of said first RF electrode when it is extended beyond said guide means.

2. A retractable RF electrode assembly as recited in claim 1 which further includes:

a) at least one other second RF electrode having a distal end and a proximal end, said second RF electrode being disposed within a second insulating sheath;

b) elongated second guide means encasing said second RF electrode and said second insulating sheath for guiding said second RF electrode into a second predetermined angle value from the longitudinal axis of said single access conduit, said second RF electrode separated from said first RF electrode by a predetermined width value;

c) said proximal end of said second RF electrode is attached to said electrode movement mechanism means, and said distal end of said second RF electrode is extendable beyond an open end of said second guide means up to a second predetermined length value so as to be engagable with and insertable into said body tissue portion;

d) said proximal end of said second RF electrode is in electrical communication with said energy source means and said tissue impedance measurement means; and e) whereby said electrode movement mechanism means moves each of said first RF and said second RF electrodes within each of associate guide means, and said distal ends of each of said first RF electrode and said second RF electrode is extendable beyond and retractable within each of said associated guide means, and when each of said distal ends of each RF electrode is extended beyond said associated guide means said energy source means is energized to pass electrical current from one RF electrode to the other and said tissue impedance measurement means measures the impedance of tissue engaged between each of said distal ends of each RF electrode.

3. A retractable RF electrode assembly as recited in claim 2, further including:

a) means for bending each of said guide means for each of said first RF electrode and said second RF electrode to vary each of said predetermined and said second predetermined angle values.

4. A retractable RF electrode assembly as recited in claim 1, further including:

a) means for bending said guide means to vary said predetermined angle value.

5. A medical probe device comprising a) a first RF electrode having a distal end and a proximal end, said first RF electrode being enclosed within an insulating sleeve, b) an elongated member having a first guide passageway disposed therein, said first RF electrode and said insulating sleeve being positioned within said guide passageway to guide said first RF electrode into a preselected angle from the central axis of said elongated member, c) an electrode positioning member attached to said first RF electrode, said distal end of said first RF electrode being extendable beyond an open end of said guide passageway up to a predetermined length and insertable into a target tissue, d) an energy source in electrical communication with said first RF electrode, and e) a tissue impedance monitoring device in electrical communication with said first RF electrode.

6. A medical probe device as recited in claim 5 which further includes a) a second RF electrode having a distal end and a proximal end, said second RF electrode being enclosed within a second insulating sleeve, b) said elongated member having a second guide passageway disposed therein, said second RF electrode and said second insulating sleeve being positioned within said second guide passageway to guide said second RF electrode into a second preselected angle from the central axis of said elongated member, said second RF electrode is separated from said first RF electrode by a third angle, c) said second RF electrode is attached to said electrode positioning member, and said distal end of said second RF electrode being extendable beyond an open end of said second guide passageway up to a second predetermined length and insertable into said target tissue, d) said second RF electrode is in electrical communication with said energy source and said tissue impedance monitoring device, and e) said electrode positioning member moves said first and second RF electrodes within said first and second guide passageways, respectively, and said distal ends of said first and second RF electrodes are extendable beyond and retractable within said first and second guide passageways, respectively, and when said distal ends of said first and second RF electrodes are extended beyond said first and second guide passageways said energy source is energized to pass electrical current from said first RF electrode to said second RF electrode, and said tissue impedance monitoring device monitors the impedance of said target tissue engaged between said distal ends of said first and second RF electrodes.

7. A medical probe device as recited in claim 6, further including a guide adjusting system coupled to said first and second guide passageways to vary the preselected angles of said first and second guide passageways.

8. A medical probe device as recited in claim 5, further including a guide adjusting system coupled to said guide passageway to vary the preselected angle of said guide passageway.

* * * * *

UNITED STATES PATENT AND TRADEMARK OFFICE
CERTIFICATE OF CORRECTION

PATENT NO. : 6,610,054 B1 Page 1 of 1
APPLICATION NO. : 08/757282
DATED : August 26, 2003
INVENTOR(S) : Stuart D. Edwards et al.

It is certified that error appears in the above-identified patent and that said Letters Patent is hereby corrected as shown below:

Col. 20, Line 50: "preselected angles" should read --preselected angle--

Col. 20, Line 51: "said first and second guide" should read --said guide--

Signed and Sealed this

Fourth Day of July, 2006

JON W. DUDAS
*Director of the United States Patent and Trademark Office*